(12) United States Patent
Bowman et al.

(10) Patent No.: US 10,653,401 B2
(45) Date of Patent: May 19, 2020

(54) MEDICAL DEVICE FOR REPAIRING SOFT TISSUE AND METHOD OF USING SAME

(71) Applicant: Smith & Nephew, Inc., Memphis, TN (US)

(72) Inventors: Steve Bowman, Sherborn, MA (US); Ruth Cheng, Natick, MA (US); Graham Smith, Newburyport, MA (US); Paul Alexander Torrie, Marblehead, MA (US)

(73) Assignee: Smith & Nephew, Inc., Memphis, TN (US)

( * ) Notice: Subject to any disclaimer, the term of this patent is extended or adjusted under 35 U.S.C. 154(b) by 1 day.

(21) Appl. No.: 15/502,624

(22) PCT Filed: Jul. 20, 2015

(86) PCT No.: PCT/US2015/041183
§ 371 (c)(1),
(2) Date: Feb. 8, 2017

(87) PCT Pub. No.: WO2016/025127
PCT Pub. Date: Feb. 18, 2016

(65) Prior Publication Data
US 2017/0224320 A1 Aug. 10, 2017

Related U.S. Application Data

(60) Provisional application No. 62/035,708, filed on Aug. 11, 2014.

(51) Int. Cl.
*A61B 17/03* (2006.01)
*A61B 17/00* (2006.01)
(Continued)

(52) U.S. Cl.
CPC ...... *A61B 17/00491* (2013.01); *A61B 17/083* (2013.01); *A61B 2017/005* (2013.01); *A61B 2090/036* (2016.02)

(58) Field of Classification Search
CPC ............... A61B 17/00491–2017/00522; A61B 17/08–2017/088
(Continued)

(56) References Cited

U.S. PATENT DOCUMENTS 4,790,819 A * 12/1988 Li ................... A61B 17/00491
604/218
4,900,303 A * 2/1990 Lemelson .......... A61B 5/02154
604/11

(Continued)

OTHER PUBLICATIONS

International Preliminary Report on Patentability from related PCT Application No. PCT/US2015/041183 dated Feb. 23, 2017.
(Continued)

*Primary Examiner* — Kathleen S Holwerda
(74) *Attorney, Agent, or Firm* — Burns & Levinson, LLP; Joseph M. Maraia

(57) ABSTRACT

A medical device for repairing soft tissue is disclosed. The medical device includes a cannulated probe positionable a tear in the soft tissue and a stop. The cannulated probe has an inlet about a proximal end and at least one outlet about a distal end with a lumen therethrough. The inlet is operatively connectable to an adhesive source to receive the adhesive therein. The outlet(s) is/are positionable about the tear to emit the adhesive about the tear. The stop is disposable about a periphery of the probe a distance from the inlet, and is positionable adjacent a surface of the soft tissue to terminate advancement of the cannulated probe into the soft tissue whereby a delivery portion of the cannulated probe is positionable about the soft tissue to deliver the adhesive about the tear.

27 Claims, 14 Drawing Sheets

(51) Int. Cl.
*A61B 17/08* (2006.01)
*A61B 90/00* (2016.01)

(58) Field of Classification Search
USPC .......................................... 606/151, 213–217
See application file for complete search history.

(56) References Cited

U.S. PATENT DOCUMENTS

| | | | | |
|---|---|---|---|---|
| 5,571,181 | A * | 11/1996 | Li | A61B 17/0057 |
| | | | | 128/DIG. 8 |
| 5,860,948 | A | 1/1999 | Buscemi | |
| 6,315,753 | B1 * | 11/2001 | Cragg | A61B 17/0057 |
| | | | | 604/15 |
| 6,475,177 | B1 * | 11/2002 | Suzuki | A61B 17/0057 |
| | | | | 604/11 |
| 6,733,515 | B1 * | 5/2004 | Edwards | A61B 17/00491 |
| | | | | 604/264 |
| 6,773,699 | B1 * | 8/2004 | Soltz | A61B 17/00491 |
| | | | | 424/426 |
| 7,850,654 | B2 * | 12/2010 | Belhe | A61B 17/0057 |
| | | | | 604/166.01 |
| 8,221,440 | B2 * | 7/2012 | Kullas | A61F 2/0063 |
| | | | | 606/151 |
| 8,945,157 | B2 * | 2/2015 | Gordon | A61B 17/0057 |
| | | | | 606/142 |
| 2002/0072745 | A1 | 6/2002 | Truckai et al. | |
| 2002/0169391 | A1 * | 11/2002 | Hung | A61B 10/0041 |
| | | | | 600/562 |
| 2002/0169477 | A1 * | 11/2002 | Demopulos | A61B 17/064 |
| | | | | 606/215 |
| 2002/0173770 | A1 * | 11/2002 | Flory | A61B 17/00491 |
| | | | | 604/537 |
| 2005/0149117 | A1 * | 7/2005 | Khosravi | A61B 17/00491 |
| | | | | 606/215 |
| 2005/0165357 | A1 * | 7/2005 | McGuckin, Jr. | A61M 25/0662 |
| | | | | 604/171 |
| 2005/0267529 | A1 * | 12/2005 | Crockett | A61B 17/00234 |
| | | | | 606/215 |
| 2006/0084368 | A1 | 4/2006 | Kapgan | |
| 2007/0255230 | A1 | 11/2007 | Gross et al. | |
| 2008/0065129 | A1 * | 3/2008 | Batchelor | A61B 18/1485 |
| | | | | 606/172 |
| 2010/0174243 | A1 | 7/2010 | McKay | |
| 2010/0274279 | A1 * | 10/2010 | Delmotte | A61B 17/00491 |
| | | | | 606/213 |
| 2013/0060334 | A1 | 3/2013 | Kurzweil | |

OTHER PUBLICATIONS

International Search Report and Written Opinion from related PCT Application No. PCT/US2015/041183 dated Nov. 3, 2015.
European Application No. 15745678.1-1122 Office Action dated Sep. 18, 2018.
Chinese Application No. 201580055176.X First Office Action dated Sep. 29, 2018.
Chinese Search Application Report No. 201580055176.X.
Australian Examination Report No. 1—Application No. 2015302209 dated Apr. 29, 2019.
Chinese Second Office Application—Application No. 201580055176.X dated Jun. 4, 2019.
Japanese Notice of Reasons for Rejection—Application No. 2017-507741 dated May 29, 2019.
Chinese Third Office Action—Application No. 201580055176.X dated Jan. 3, 2020.
Chinese Search Report—Application No. 201580055176.X.

* cited by examiner

800 - METHOD OF REPAIRING SOFT TISSUE

---

840 - PROVIDING A CANNULATED PROBE HAVING AN INLET AT A PROXIMAL END AND AT LEAST ONE OUTLET ABOUT A DISTAL END WITH A LUMEN THERETHROUGH

↓

842 - DISPOSING A STOP ABOUT A PERIPHERY OF THE PROBE A DISTANCE FROM THE INLET

↓

844 - POSITIONING A CANNULATED PROBE ABOUT A TEAR IN THE SOFT TISSUE

- INSERTING A TIP OF THE CANNULATED PROBE INTO THE TEAR,
- PASSING THE CANNULATED PROBE THROUGH THE TEAR BY INSERTING A TIP OF THE CANNULATED PROBE THROUGH THE SOFT TISSUE ON EITHER SIDE OF THE TEAR, AND/OR
- BRIDGING THE TEAR BY EXTENDING THE CANNULATED PROBE THROUGH SOFT TISSUE ON EITHER SIDE OF THE TEAR.

↓

846 - TERMINATING ADVANCEMENT OF THE CANNULATED PROBE ABOUT THE SOFT TISSUE BY POSITIONING THE STOP ADJACENT A SURFACE OF THE SOFT TISSUE

↓

848 - DELIVERING THE ADHESIVE ABOUT THE TEAR BY PASSING AN ADHESIVE FROM THE INLET, THROUGH THE LUMEN, AND OUT THE AT LEAST ONE OUTLET

↓

850 - PASSING THE ADHESIVE OUT A PLURALITY OF THE AT LEAST ONE OUTLETS AND INTO THE TEAR

↓

852 - SEALING THE TEAR WITH THE STOP

↓

854 - DISPOSING A FIBER OPTIC THROUGH THE CANNULATED PROBE AND VISUALIZING THE SOFT TISSUE

↓

856 - CLIPPING THE SOFT TISSUE AND DISPOSING THE CANNULATED PROBE THROUGH THE CLIPPED SOFT TISSUE

↓

858 - RETRACTING THE CANNULATED PROBE FROM THE SOFT TISSUE

*FIG. 8*

MEDICAL DEVICE FOR REPAIRING SOFT TISSUE AND METHOD OF USING SAME

CROSS-REFERENCE TO RELATED APPLICATIONS

This application is the U.S. National Stage of International Application No. PCT/US2015/041183, filed on Jul. 20, 2015, which claims the benefit of U.S. Provisional Application No. 62/035,708 filed on Aug. 11, 2014, the entire contents of the above-identified applications are incorporated herein by reference in their entirety.

BACKGROUND

The present disclosure relates to devices and methods for their use for delivering bioadhesives (also referred to herein as "adhesives") to sites in a body in need of repair, such as in reattachment or reinforcement of soft tissue tears (e.g., meniscal tears), ligament and muscle reattachment to bone, sealing joint capsules, and repairing cartilage delamination. Some embodiments of the disclosure may have particular use in minimally invasive orthopedic surgery, such as in delivering adhesives to sites in confined joint spaces, such as a meniscus and other difficult to reach anatomy.

By way of non-limiting example only, certain embodiments of the device and methods relate to reattaching and/or repairing meniscal tears. For non-limiting example, meniscal tissue in the knee may develop a longitudinal, vertical lesion, sometimes referred to as a "bucket handle" lesion. It is recognized that such lesions will heal over time if the lesion is closed and stabilized. One known method for repairing a meniscus tear includes making an incision accessing the knee joint and the torn meniscus; placing a suture into an inner portion of the torn meniscus and drawing it through to the outer portion. The suturing may be repeated until the tear is closed as tightly as desired. Another procedure of closing tissue tears, such as meniscal tears, involves the use of a pair of long needles which contain a suture between them, and placing the two needles through the torn meniscus from the front of the knee joint exiting percutaneously from the posterior area of the joint.

However, the use of sutures in repairing tissue tears, such as meniscal tears, is known to have deficiencies and complications, such as when sutures and/or suture knots press or rub against adjacent tissue, causing irritation. Additionally, pathologic or otherwise compromised tissue near the tear edge(s) can experience suture drag, or "cheese wiring," potentially reducing the efficacy of the repair.

Other meniscal repair (for example) systems use a fastener which is proposed to be inserted arthroscopically. In one system, the fastener has a shank, an enlarged head at one end of the shank, and one or more barbs at the other end and/or spaced along the length of the shank. The barbed end of the fastener is tapered to a point. The fastener is proposed to be inserted, pointed end first, into the interior region of a meniscus adjacent to a tear. Insertion of the fastener can require complicated insertion devices and methods due, for example, to the barbed nature of the fasteners. Insertion is continued until the enlarged head of the fastener engages meniscal tissue. The length of the shank is selected so that when fully inserted (i.e., when the enlarged head of the fastener engages meniscal tissue), the tapered, barbed end of the fastener penetrates the meniscal tissue on the opposite side of the meniscus tear; thus, the fully inserted fastener bridges the gap of the tear and is engaged with meniscal tissue at both sides of the tear. The barbs are purportedly intended to prevent retraction of the fastener so that the meniscal tear is permanently held in the bridged position; it is further purported that the tear will eventually fully heal as repair tissue fills in the gap between the tears edges.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In at least one aspect, the disclosure relates to a medical device for repairing soft tissue is disclosed. The medical device includes a cannulated probe positionable a tear in the soft tissue and a stop. The cannulated probe has an inlet about a proximal end and at least one outlet about a distal end with a lumen therethrough. The inlet is operatively connectable to an adhesive source to receive the adhesive therein. The outlet(s) is/are positionable about the tear to emit the adhesive about the tear. The stop is disposable about a periphery of the probe a distance from the inlet, and is positionable adjacent a surface of the soft tissue to terminate advancement of the cannulated probe into the soft tissue whereby a delivery portion of the cannulated probe is positionable about the soft tissue to deliver the adhesive about the tear.

In another aspect, the disclosure relates to a system for repairing soft tissue. The system includes an adhesive stored in an adhesive source, and a medical device. The medical device includes a cannulated probe positionable a tear in the soft tissue and a stop. The cannulated probe has an inlet about a proximal end and at least one outlet about a distal end with a lumen therethrough. The inlet is operatively connectable to an adhesive source to receive the adhesive therein. The outlet(s) is/are positionable about the tear to emit the adhesive about the tear. The stop is disposable about a periphery of the probe a distance from the inlet, and is positionable adjacent a surface of the soft tissue to terminate advancement of the cannulated probe into the soft tissue whereby a delivery portion of the cannulated probe is positionable about the soft tissue to deliver the adhesive about the tear.

In yet another aspect the disclosure relates to a method of repairing soft tissue. The method involves providing a cannulated probe having an inlet at a proximal end and at least one outlet about a distal end with a lumen therethrough, disposing a stop about a periphery of the probe a distance from the inlet; positioning a cannulated probe about a tear in the soft tissue; terminating advancement of the cannulated probe about the soft tissue by positioning the stop adjacent a surface of the soft tissue; and delivering the adhesive about the tear by passing an adhesive from the inlet, through the lumen, and out the outlet.

Finally, in another aspect, the disclosure relates to a method of repairing soft tissue. The method involves providing the medical device, inserting the cannulated probe into the soft tissue, passing the adhesive through the lumen and into the tear, and retracting the cannulated probe from the soft tissue.

The disclosure also relates to a medical device for at least partially adhesively repairing a soft tissue tear comprising a cannulated probe having a proximal end and opening and a distal end and opening; at least one lumen within the cannulated probe having a proximal opening and a distal opening; the cannulated probe shapeable to lie over a healthy soft tissue surface near a soft tissue tear to be at least partially adhesively sealed; the cannulated probe shapeable to place the distal end of the cannulated probe into the soft tissue tear to be at least partially adhesively sealed; and an adhesive delivery source engageable with the proximal opening of the lumen and engageably forming a fluid flow pathway from the adhesive delivery source to the distal opening of the lumen.

The medical device may also include a second lumen within the cannulated probe. The second lumen may extend partially through the cannulated probe from a proximal opening of the second lumen to a distal termination of the second lumen located before the distal end of the cannulated probe. The second lumen may contains a guide wire and is a blind lumen. The second lumen may merge into the lumen at the distal termination of the second lumen forming a common lumen proximate the distal end of the cannulated probe. The adhesive may include a two component adhesive and one of each component is contained within each separate lumen and merge together in the common lumen. The tissue may be a meniscus and the tear may be a meniscal tear.

The disclosure also relates to a method of administering a tissue adhesive to a meniscal tissue tear comprising using a device according to claim 1 to deliver an adhesive to a meniscal tear. The cannulated probe may be shapeable for placement upon at least a portion of meniscal tissue near the meniscal tear, and the distal end of the cannulated probe is shapeable for placement within the meniscal tear. The cannulated probe may also include a second lumen with a proximal opening proximate the proximal end of the cannulated probe and a distal opening proximate the distal end of the cannulated probe. The adhesive may include a two component adhesive and one of each component is delivered to each separate lumen. The cannulated probe may include a second lumen extending partially through the cannulated probe from a proximal opening proximate the proximal end of the cannulated probe and a distal termination of the second lumen located before the distal end of the cannulated probe, the second lumen being a blind lumen reversibly containing a guide wire for manipulating the cannulated probe. The cannulated probe may also include at least one polymer and/or metal imparting shapeability to the cannulated probe.

The disclosure also relates to a medical device for repairing a soft tissue tear comprising: a cannulated probe having a tubular wall, a distal end, and a proximal end and opening; at least one lumen within the cannulated probe having a proximal opening; side ports through the tubular wall opening between and providing communication between an environment external to the cannulated probe and an environment within the lumen; a depth stop having an external diameter greater than an external diameter of the cannulated probe, attachable to an exterior surface of the tubular wall at a position where the side ports are distal to the drill stop and where on insertion from the distal end of the cannulated probe the depth stop meets an outer surface of soft tissue to be treated such that the cannulated probe is insertable to a position where the cannulated probe bridges the tear and the side ports are located within the tear; and at least one adhesive delivery source associable with the proximal opening of the lumen, assoicably forming a communication between the adhesive delivery source, the lumen and the environment exterior to the cannulated probe through the side ports.

The cannulated probe may also include at least one material that imparts limited flexibility to the cannulated probe. The side ports may be angled to deliver the adhesive into the tear. The cannulated probe is removable after being inserted into the soft tissue to be treated.

The disclosure also relates to a method of repairing a soft issue tear with an adhesive using the medical device. The depth stop may be adjustably locatable on the exterior surface of the tubular wall of the cannulated probe to a position where the depth stop meets an outer surface of the tissue to be treated such that the cannulated probe is inserted to a position within the tissue where the cannulated probe bridges the tear and the side ports are located within the tear. The side ports may deliver the adhesive into the tear and not into surrounding tissue. The may also involve inserting the cannulated probe into and through an area of non-pathologic soft tissue near the tear; approaching with the cannulated probe the tear in an orientation that is generally perpendicular to the length of the tear; entering with the cannulated probe the tear through a wall of the tear; exiting with the cannulated probe the tear through an opposing wall of the tear; and entering with the cannulated probe a region of non-pathologic tissue near the tear. The cannulated probe may be stabilized across the tear by its location in the non-pathologic tissue near the tear.

Biologically compatible adhesives (bioadhesives) have been used to close superficial skin wounds and surgical incisions. Adhesives have also sometimes been used internally for aiding in soft tissue repair in non-load bearing applications. However, the use of adhesives in sports medicine and orthopedics has been limited due to inferior properties of earlier adhesives, for example, lack of sufficient strength for repairs in loadbearing applications, and insufficient elasticity for musculoskeletal tissue which undergoes flexion, compression, torsion, and shear forces.

Newer surgical adhesives have been, and are being developed that address these deficiencies; however, there remains a need for devices, and methods for their use, for administering bioadhesives including their internal administration, for example, in sports medicine and orthopedics. Such devices and methods for their use include for administering bioadhesives, for example but not limited to, in reattachment and/or reinforcement of loadbearing soft tissue tears (such as, for example, meniscal tears), loadbearing ligament and muscle reattachment to bone, sealing joint capsules, and repairing cartilage delamination. As noted above, some embodiments disclosed may have particular use in minimally invasive orthopedic surgery, such as in delivering adhesives to confined joint spaces and other difficult to reach internal anatomy; for example, for the administration of bioadhesives for the reattachment, and/or reinforcement of a repair to, a meniscal tear in the knee.

Some embodiments of the disclosure relate to devices, and methods of their use, for the injection or spraying of an adhesive(s) to a site in need of repair, such as a tear in a meniscus, via a cannulated probe, or needle, having one or more lumina, and being flexible or inflexible.

In certain embodiments, the disclosure relates to a cannulated probe having a planar surface extending substantially radially from the outer surface of the probe and adjustable for location substantially flat and/or flush against a superior meniscal surface above a tear to be repaired. When injecting (and/or spraying)—wherein throughout this application the terms "injecting," "injection," and the like may be used interchangeable with the terms "spraying," "spray," and the like (unless the context indicates that a specific term is intended)—an adhesive into a soft tissue tear with such a device or method, the planar surface assures that the edges of the superior meniscal tear are aligned substantially smoothly and/or flush with the superior meniscal surface above a tear. The planar surface may also prevent excess adhesive from exiting the surface of the tear, and/or allow for detection of sufficient (or insufficient) supply of adhesive to the tear, for example, to fill the tear.

In other embodiments, one or more lumina in the cannulated probe (needle) may provide, for example, separate passages for the injection of a single-component adhesive, a multi-component adhesive (e.g., injected via separate lumina for separate components to a desired site in vivo and mixed at the site of application), one or more adhesives and one or more additional agents (such as bioactive agents, including but not limited to growth factors, angiogenic factors, antibiotics, and the like), one or more adhesives and an optical fiber, and the like.

In further embodiments of the disclosure, a cannulated needle is designed to pierce both sides of a soft tissue tear, perhaps but not necessarily thereby stabilizing the tear prior to, during, and/or after administration of adhesive. In embodiments of the invention, one or more adhesives are then injected or sprayed into the tear by side ports on the needle located within the tear itself (i.e., in the region spanning/bridging the tear). In embodiments having these side ports, embodiments of the invention may also have injection spaces located in one or both regions of the needle that are located within the tissue lining the tear (e.g., those areas of the needle located within the tissue near bridged sides of the tear). Embodiments of the invention also include devices, systems, and methods wherein a the needle having the side ports for injection of adhesives into a tear, one or both regions of the needle located in one or both areas of the tissue bridged by the needle may not also inject adhesive into the tissue on one or both side(s) of the tear.

By non-limiting illustration, in embodiments discussed immediately above wherein the needle or probe has side ports and injects adhesive into a tear, and also has openings for injection adhesive into tissue near one or both edges of the bridged tear, the injection of adhesive into one or both regions of tissue may assist in anchoring the probe while it is bridging the tear (however, in these embodiments, as well as others herein, the probe or needle may be (but not necessarily is) withdrawn from the repaired tissue after the adhesive administration).

In the non-limiting embodiments discussed immediately above wherein the needle or probe has side ports and injects adhesive into a tear, but does not have openings in or inject adhesive from one or both regions of tissue near the edges of the bridged tear, the lack of injection may (but not necessarily is) be to avoid possible irritation of the tissue near the tear and/or to assist in removal of the needle following adhesive administration.

In further embodiments of the invention, in order to assist that the needle is inserted into both sides of a tissue tear (and/or to assist that the needle's side ports are correctly placed for delivery of adhesive(s) within (and/or in the tissue near the edge of) the tear), the cannulated needle may have a slidable depth stop, such as a planar, disk-like surface extending radially or at an angle from the outer surface of the needle.

In still further embodiments, a cannulated probe may have plates that clamp on each planar side (e.g., femoral and tibial) of a meniscus having a tear to be repaired. This ensures that, by non-limiting example, the injection of the adhesive is contained between the planar surfaces and/or that the edges of the tear once repaired are properly oriented with the surface of the surrounding tissue (e.g., that the edges of the repaired tear are substantially flat and/or smooth to the surface of the surrounding menisci). The plates may, for example, be fixed at a distinct angle relative to each other, be capable of having a fixed angle to each other that may be adjustably fixed (or changed), for example, by bending the portion of the clamp connecting the top and bottom plates, or the top and bottom plates may be hinged to allow for a range of angles (which may or may not be fixed).

Additional embodiments of the Invention include a microneedle array at the tip of the cannulated needle with, for example, a single deployment mechanism to deliver adhesive simultaneously to multiple locations within a delivery site, such as within a soft tissue tear.

Still further, embodiments of the Invention may include the use of the device with a multiple arm manipulator that uses piercing arms or needles, or suction, to bring tissue on opposing sides of a tear together to adhere (or be assisted in adhering) via injected adhesive.

Fiber-optics may also be included in embodiments of the Invention. For example, optical fibers may be incorporated onto, or adjacent to, the tip of the cannula, or through a lumen within the cannula. All, or virtually all, of the embodiments discussed herein may have at least one optical element to, for example, assist in visualizing (e.g., by eye and/or machine) the application of adhesive.

Additional embodiments of the Invention include but are not limited to devices for the delivery of thin adhesive sheets to surgical sites in need of adhesion. For example, thin adhesive sheets may be packaged and delivered by a cannulated probe to a site of a tissue tear, such as a soft tissue tear, such as a meniscal tear, then cut to fit the size of the tear area during a procedure.

An embodiment of the invention relates to a medical device for at least partially adhesively sealing a soft tissue tear, the device having (for example, but not by limitation): a cannulated probe having a proximal end and opening and a distal end and opening; at least one lumen within the cannulated probe having a proximal opening and a distal opening; the cannulated probe shapeable to lie over a healthy tissue surface near a soft tissue tear to be at least partially adhesively sealed; the cannulated probe shapeable to place the distal end of the cannulated probe into the soft tissue tear to be at least partially adhesively sealed; an adhesive delivery source reversibly or irreversibly engageable with the proximal opening of the lumen, engageably forming a fluid flow pathway from the adhesive delivery source to the distal opening of the lumen. Adhesive delivery sources of embodiments of the invention described throughout include, without limitation, any and all devices, systems, methods, and the like capable of delivering one or more adhesives to the medical devices, instruments, systems and the like described herein and/or for their uses in the methods and the like described herein. Adhesive delivery sources include those known or knowable in the art.

By non-limiting example, an adhesive delivery source may include one or more components or devices provided that the adhesive delivery source meets the above description. For non-limiting example, an adhesive delivery source may include a device for injecting an adhesive, with or without one or more tubes or other parts, components, devices, or the like that may extend, alter, or the like, for example, the location of the output from the adhesive delivery source to the distal opening of the lumen.

By non-limiting example, an adhesive delivery source of embodiments of the invention may be a syringe that is reversibly or irreversibly engageable, associable, and the like with the proximal opening of the lumen. Further, by non-limiting example, the adhesive delivery source of embodiments of the invention may be a syringe having attached (attachable, and the like) reversibly or irreversibly thereto one or more tubes (such as one or more injection tubes), wherein the syringe and the tube(s) is/are the adhesive delivery source that is reversibly or irreversibly engageable, associable, and the like with the proximal opening of the lumen (in this non-limiting example, the adhesive delivery source may be engageable, e.g., via an end of a tube within the adhesive delivery source). Another non-limiting example of the present invention is the medical instrument described in the preceding paragraph, further having a second lumen within the cannulated probe.

Still further, for example, in the medical device of the previous two paragraphs the second lumen may extend partially through the cannulated probe from a proximal opening of the second lumen to a distal termination of the second lumen located before the distal end of the cannulated probe.

Additionally, in the medical instrument described in the above three paragraphs, the second lumen may contain a guide wire and be a blind lumen. Also, in the medical instrument of the preceding three paragraphs the second lumen may merge into the lumen at the distal termination of the second lumen, thereby forming a common lumen proximate the distal end of the cannulated probe.

In yet further embodiments, in the medical device described in the preceding four paragraphs, the adhesive can be a two component adhesive and one of each component can be contained within each separate lumen, and merge together in the common lumen.

In additional embodiments of the invention, the tissue can be a meniscus and the tissue tear can be a meniscal tear.

In other embodiments, the invention relates to methods of administering a tissue adhesive to a meniscal tissue tear by using the above described device according to deliver an adhesive to a meniscal tear.

In such methods, the cannulated probe of the medical instrument may be shapeable for placement upon at least a portion of meniscal tissue near the meniscal tear, and the distal end of the cannulated probe may be shapeable for placement within the meniscal tear.

In additional methods, the cannulated probe may have a second lumen with a proximal opening proximate the proximal end of the cannulated probe and a distal opening proximate the distal end of the cannulated probe. In such embodiments, the adhesive may be a two component adhesive and one of each component can be delivered to each separate lumen.

Still further, in the methods of the invention, the cannulated probe may have a second lumen extending partially through the cannulated probe from a proximal opening proximate the proximal end of the cannulated probe, and a distal termination of the second lumen located before the distal end of the cannulated probe, the second lumen being a blind lumen reversibly containing a guide wire for manipulating the cannulated probe.

Still further, in devices used in embodiments of the methods of the invention, the cannulated probe may be made, at least in part, of at least one polymer and/or metal imparting shapeability to the cannulated probe.

Further exemplary embodiments of the invention relate to medical devices for sealing a soft tissue tear wherein the devices have at least: a cannulated probe having a tubular wall, a distal end, and a proximal end and opening; at least one lumen within the cannulated probe having a proximal opening; side ports through the tubular wall opening between and providing communication between an environment external to the cannulated probe and an environment within the lumen; a depth stop having an external diameter greater than an external diameter of the cannulated probe, attachable to an exterior surface of the tubular wall at a position where the side ports are distal to the drill stop and where on insertion from the distal end of the cannulated probe the depth stop meets an outer surface of soft tissue to be treated such that the cannulated probe is insertable to a position where the cannulated probe bridges the tear and the side ports are located within the tear; and at least one adhesive delivery source associable with the proximal opening of the lumen, associably forming a communication between the adhesive delivery source, the lumen, and the environment exterior to the cannulated probe through the side ports. The association of the adhesive delivery source (e.g., as discussed above wherein the adhesive delivery source may be of any number or component(s), device(s), and the like capable of injecting at least one adhesive in the embodiments described throughout, for non-limiting example, the adhesive delivery source in some embodiments may be a syringe, or may be a syringe attached to a delivery tube) with the distal opening of the lumen may be reversible or irreversible.

Additionally, the medical devices of some of the embodiments of the invention, including of some of the devices and methods described in the paragraphs within (but not necessarily limited to) this Summary, the cannulated probe may further have at least one shapeable region which region can, for non-limiting example, extend the length of the probe, or be located in one or more regions along the cannulated probe; the shapeable region containing at least one material that imparts limited flexibility to the cannulated probe.

Further, the medical device as described, for non-limiting example, in the illustrative embodiments of the two prior paragraphs, wherein the side ports of the cannulated probe are angled to deliver the adhesive into the tear to be adhesively sealed.

Additionally, in the medical devices as described, for non-limiting example, in the illustrative embodiments of three prior paragraphs, the cannulated probe is removable after being inserted into the soft tissue to be sealed.

Further for non-limiting examples, embodiments of the invention include methods of using the medical device (e.g., but not by limitation, as the device is described in the immediately preceding paragraphs) for repairing a soft tissue tear with an adhesive.

Other aspects of the invention disclosed and described herein relating, for example, to the method as described in the preceding paragraph, include wherein the depth stop of the medical device is adjustably located on the exterior surface of the tubular wall of the cannulated probe at a position where the depth stop meets an outer surface of the tissue to be treated such that the cannulated probe is inserted to a position within the tissue where the cannulated probe bridges the tear and the side ports are located within the tear. In this method, for example, the side ports can deliver the adhesive into the tear and not to surrounding tissue.

Still further exemplary embodiments of methods of using the medical devices (e.g., but not by limitation, as the devices are described in the preceding Summary and all aspects are described in more detail below) for repairing a soft tissue tear with an adhesive include: inserting the cannulated probe into and through an area of non-pathologic soft tissue near the tear; approaching with the cannulated probe the tear in an orientation that is generally perpendicular to the length of the tear; entering with the cannulated probe the tear through a wall of the tear; exiting with the cannulated probe the tear through an opposing wall of the tear; entering with the cannulated probe a region of non-pathologic tissue near the tear; and wherein the cannulated probe is stabilized across the tear by its location in the non-pathologic tissue near each side of the tear.

BRIEF DESCRIPTION OF THE DRAWINGS

So that the above recited features and advantages of the disclosure can be understood in detail, a more particular description of the disclosure, briefly summarized above, may be had by reference to the embodiments thereof that are illustrated in the appended drawings. It is to be noted, however, that the appended drawings illustrate only illustrative embodiments of this disclosure and are, therefore, not to be considered limiting of its scope. The figures are not necessarily to scale, and certain features and certain views of the figure may be shown exaggerated in scale or in schematic in the interest of clarity and conciseness.

FIG. 8 is a flow chart depicting a method of sealing soft tissue.

DETAILED DESCRIPTION

The description that follows includes exemplary apparatuses, devices, materials, methods, techniques, and the like that embody techniques of the inventive subject matter. However, it is understood that the described embodiments may be practiced without these specific details and that the invention is not necessarily limited to these details.

The disclosure relates to devices, systems, and methods for repairing tissue tears, such as soft tissue tears. Such devices are delivery devices for use with materials, such as bioadhesives delivered by cannulated probes (or needles or tubular components). For example, the cannulated probes may have a lumina for delivering multi-component adhesives separately through the device in order for adhesive to mix and form in situ (e.g., site-specifically). The cannulated probes may be used to bridge tears to be adhered and deliver adhesive into the tear. The cannulated probes may be used, for example, for repairing orthopedic and sports medicine injuries, including in load bearing applications and/or those in difficult to access spaces such as meniscal tears without the need for open surgery.

Figure 1:
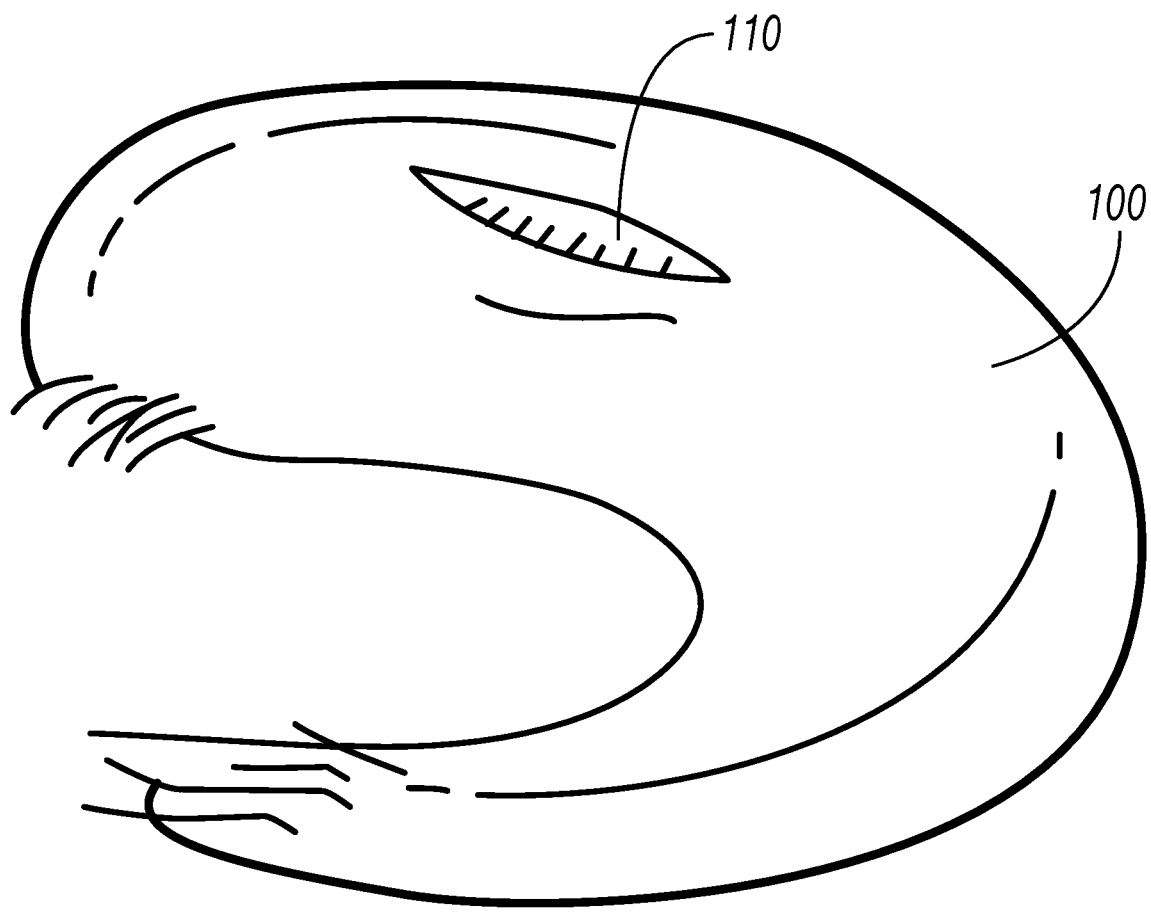
FIG. 1 is a perspective view showing a meniscus tear in soft tissue.

FIG. 1 shows an exemplary perspective view a meniscus 100, such as medial meniscus, having a tear 110, of a type that can be repaired in accordance with embodiments of the instant devices, systems, and methods.

Figure 2:
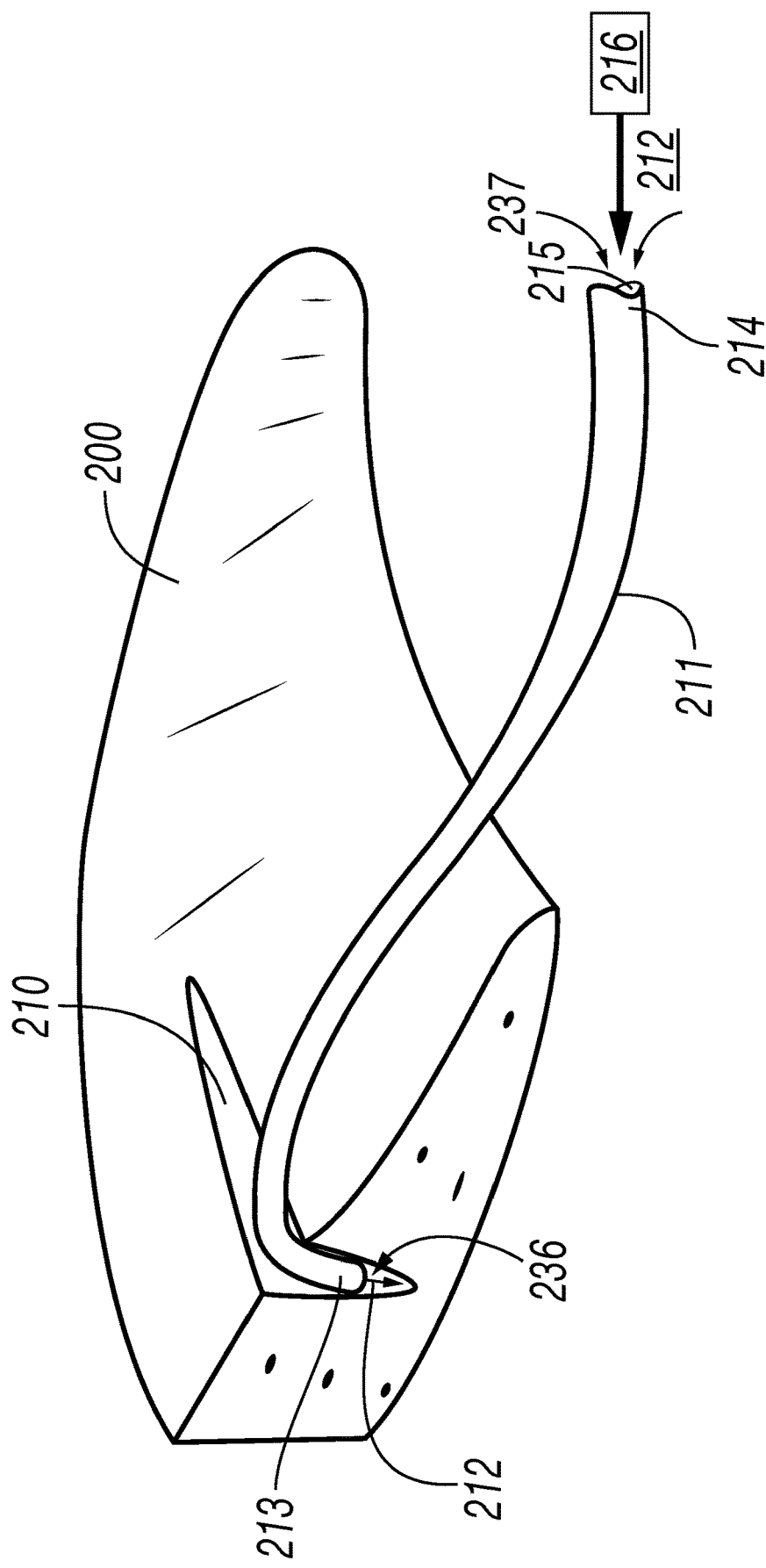
FIG. 2 is a perspective view showing an embodiment of the invention wherein a tubular component (e.g., cannulated probe) is capable of delivering an adhesive into a tissue tear, such as a meniscus tear.

FIG. 2 shows an embodiment of the invention wherein a hollow or cannulated probe 211 is used to deliver (inject, administer, spray, or the like) at least one adhesive 212 from a source 216 of the one or more adhesive 212 into a tear 210 in a soft tissue, such as a tear in the medial meniscus 200.

The hollow or cannulated probe 211 is elongated and has a distal end and opening 213 and a proximal end and opening 214. The hollow or cannulated probe has at least one lumen 215. In some embodiments the one or more lumen(a) 215 extend(s) the length of the probe 211, and has at least a distal opening 236 proximate the distal end and opening 213 of the cannula 211 and at least a proximal opening 237 proximate the proximal end and opening 214 of the cannula 211.

While multiple lumina within the probe are not shown, they are understood to be within the scope of this disclosure, including that they may extend the length of a cannulated probe as does the lumen 215 shown in FIG. 2.

The source 216 of the one or more adhesive 212 may be any suitable source, including but not limited to a manual or an automated (e.g., programmable) pump, a syringe, gravity feed, or any other pressurized or otherwise powered delivery mechanism, or the like. Further, for non-limiting example, adhesive material can be dispensed in predetermined amounts (e.g. a predetermined volume with each depression of a trigger (not shown) associated with the source 216 of the one or more adhesive(s) 212, or for example continuously dispensed as long as the trigger is activated.

The source 216 of the one or more adhesive 212 may be configurable to reversibly or irreversibly couple (not shown) with the lumen(a) 215 at the distal end 214 of the probe; for example, to form a fluid connection between the source 216 of the one or more adhesive 212 and the lumen(a) 215 at the distal end 214 of the probe.

Figure 2A:
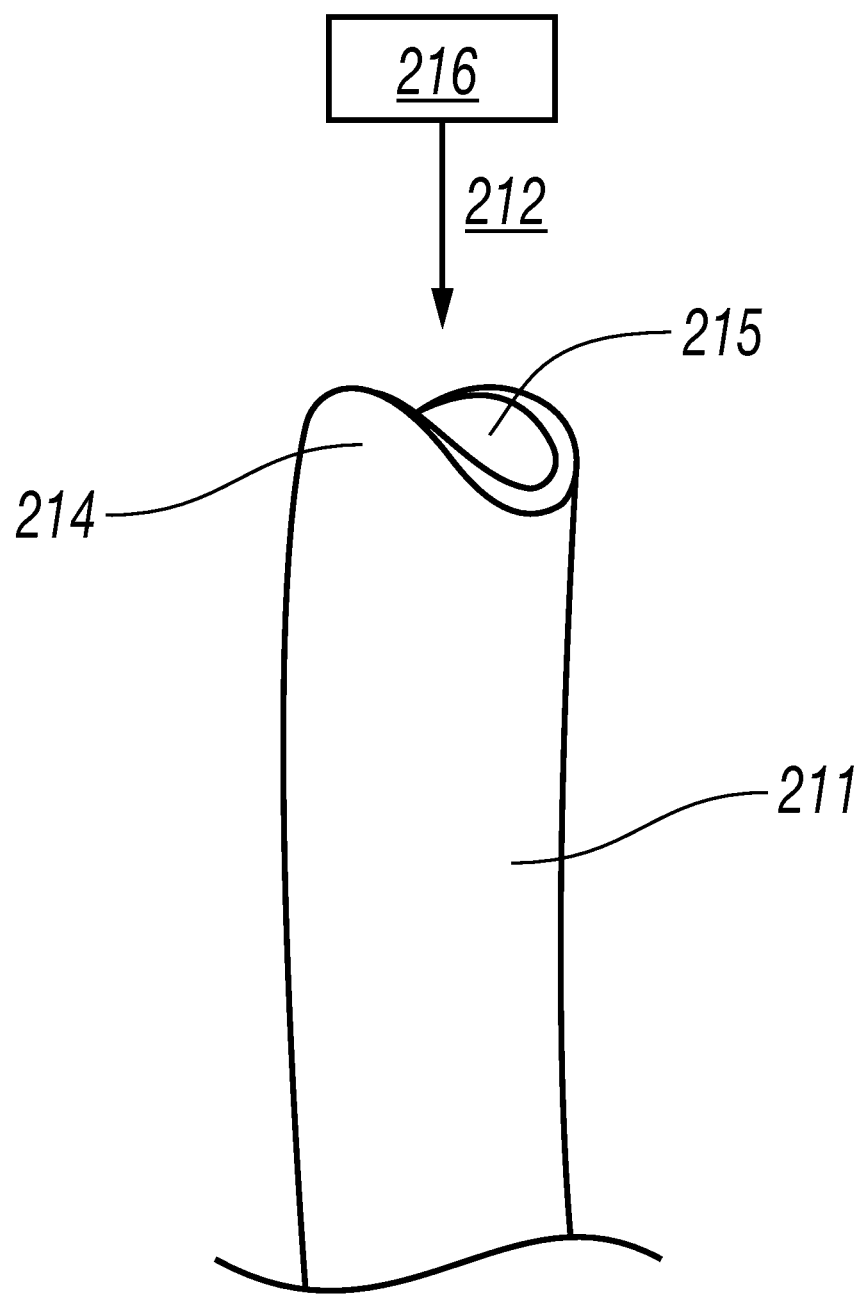
FIG. 2A is a partial view of FIG. 2 showing an enlarged perspective view of the proximal end of the hollow or cannulated probe.

FIG. 2A is a partial view of FIG. 2 showing an enlarged perspective view of the proximal end 214 of the hollow or cannulated probe 211, showing the one or more lumen(a) 215, and the source 216 of the one or more adhesive 212, as shown in FIG. 2.

The adhesive(s) used in the invention are not limited and include all of those known and knowable in the art for use with embodiments of the instant invention. This includes but is not limited to all known and knowable biocompatible adhesives, including for example resorbable and non-resorbable adhesives, multicomponent adhesives, and adhesives containing added agents. Certain embodiments of the inventions disclosed and described herein may preferably be used with adhesives having particular applicability for use in orthopedic and sports medicine, such as those having particular strength and elasticity for adhering musculoskeletal tissue which undergoes flexion, compression, torsion, and shear forces.

In certain embodiments of the invention, the adhesive(s) used are those having the ability to repair or assist in repairing (e.g., in association with suturing) reattachment or reinforcement of soft tissue tears (e.g., meniscal tears), ligament and muscle reattachment to bone, sealing joint capsules, and repairing cartilage delamination. Adhesives for use with certain embodiments of the disclosure may have particular use in minimally invasive orthopedic surgery, such as in delivering adhesives to sites in confined joint spaces and other difficult to reach anatomy, such as to a meniscus in the knee.

While adhesives having certain properties beneficial to use in orthopedic and sports medicine, some of which are discussed above, the devices, systems, and methods of the invention include the use of any adhesives that are compatible with the disclosed device (e.g., having or capable of having some degree of flowability at or near the body temperature of an animal to be treated), known or knowable in the art. This includes adhesives that might not, for example, be sufficiently strong for single use in an application of the invention (such as in adhering a meniscal tear), but are in combination with, for example, other adhesives, agents, and/or attachment techniques (such as in combination with suturing). Further, for non-limiting example, certain embodiments of the invention, such as those wherein a needle or probe spans a tear to be repaired (thereby, for example, stabilizing the tear), may not require adhesives with notably strong adhering capability.

Exemplary adhesives for use with the disclosed and described devices, systems, and methods include, but are not limited to single or multi-part adhesives that are polymerizable and/or cross-linkable; for example, cyanoacrylate adhesives. The adhesive can be fluid and for example, may be a monomeric (including prepolymeric) adhesive composition, a polymeric adhesive composition, or any other natural or artificial biocompatible compounds that can adhere to tissue. In embodiments, the monomer may be a 1,1-disubstituted ethylene monomer, for example, an α-cyanoacrylate. Such adhesives (and others) may be flowable and crosslinkable at the site of adhesion. When cross linked, the cyanoacrylate may change from a liquid to a solid. Cross linked adhesive can range from rigid to flexible and can be non-permeable or permeable. If desired, adhesive may be a single part or dual part adhesive, and/or can contain one or more additives. For multipart adhesives, they may be delivered to a repair site via a device having at least two lumina, each of which carries a component separately, and the components meet upon delivery at the application site.

In some embodiments, the individual components are flowable while the multicomponent adhesive mixture is not. Multicomponent adhesive mixtures may be polymerized by moisture, blood, saline, or adhesive initiators, or other agents or physical treatments, such as by exposure to certain wavelengths of light, which may be delivered by an optical fiber associated with a device (for example, supplied within a separate lumen). Crosslinking in situ may also be facilitated by such exposure to light at the site of application. Adhesive initiators may also be used to set up or polymerize an adhesive, and can be but are not necessarily base compounds and the like.

Adhesives may also contain suitable chemical agents such as anesthetic agents, plasticizing agents, therapeutic agents, buffers, catalysts, fillers, micro particles, adhesion initiators, thickeners, solvents, drugs, medicaments, natural and/or synthetic rubbers, stabilizers, pH modifiers, bioactive agents, cross-linking agents, chain transfer agents, fibrous reinforcements, colorants, preservatives, reducing or scavenging agents such as formaldehydes, mixtures thereof, and the like.

Still further, any by non-limiting example, the adhesive material may be a formulation of one or more biocompatible materials such as polymers. Adhesive material may be made of materials which will remain intact, permanently implanted over long periods of time, such as times greater than 6 months. Alternatively, adhesive material may be made of materials which remain active for a suitable amount of time to allow tissue regrowth/reattachment, but then bioabsorb; this may include those having a bioabsorption rate of less than six months, less than 1 month, less than seven days, or essentially any amount of time which is suitable for the intended use of the adhesive in situ. Numerous materials have been developed to be absorbed by the body, such as a magnesium reinforced polymer. Numerous polymers can be used such as polylactide, poylglycolide, polysaccharides, certain proteins, polyesters, polyhydroxyalkanoates, polyalkelene esters, polyamides, polycaprolactone, polyvinyl esters, polyamide esters, polyvinyl alcohols, polyanhydrides and their copolymers, modified derivatives of caprolactone polymers, polytrimethylene carbonate, polyacrylates, polyethylene glycol, polyolefin, engineered materials, hydrogels, photo-curable hydrogels, terminal diols, minerals, and combinations of these. Bioabsorbable fibers that reinforce a bioabsorbable polymer matrix may also be used in certain embodiments. Such adhesives, and others, can be made in permanent or absorbable matrices and can include minerals and therapeutics as one or more of the constituents.

In some embodiments, the adhesive material includes two separate substances. The substances may be mixed prior to placing in device and then delivered to the desired site via a single lumen, may be mixed within a device, such as with an embodiment of the device having a single lumen into which both components are injected at (for example) the proximal end and mix while being injected, and for example, by a device having at least two lumina that extend separately to open into (merge into) a common lumina within the cannula and for example located toward distal end of the cannula, wherein the components mix in the cannula before being injected into a surgical site. Multicomponent adhesives, and/or multiple separate adhesives, may also be injected separately into a surgical site by the use of a device having multiple lumina, at least one for each separate component. The two or more separate substances may have different bioabsorption rates, different long term rigidity, or other different pre or post dispensing properties, including flowability wherein single components are flowable yet the mixture formed in situ is not. In certain embodiments, adhesive material(s) may include three or more different substances. In embodiments adhesive material can be combined, for example in situ with a permanent or absorbable portion; for example, allowing the adhesive to be flowable through the cannula and then non-flowable when mixed with the other component in situ.

In certain embodiments, the disclosure relates to a cannulated probe having a planar surface (or stop) extending substantially radially from the outer surface of the probe and adjustable for location substantially flat and/or flush against the superior meniscal surface above a tear to be repaired. When injecting (spraying, or the like) an adhesive into a soft tissue tear with such a device, system, or method, the planar surface assures that the edges of the superior meniscal tear are aligned substantially smoothly and/or flush with each other and with the superior meniscal surface above the tear. This may be done, for example, to help prevent an over accumulation of adhesive at the treatment size, which otherwise may produce, for example, an adhesive and/or tissue bulge in the meniscal surface above the tear compared to the superior meniscal surface surrounding the area of the tear. In embodiments of the invention, the planar surface may also provide for detection of sufficient (or insufficient) supply of adhesive to the tear, for example, to determine whether a sufficient amount of adhesive has been added to suitably fill the tear. In embodiments wherein the planar surface acts to provide for detection of the amount of adhesive added, optical fibers and the like my be included in lumen(a) of the cannula, or otherwise associated with the device, to provide visual and/or automated detection of an amount of adhesive added to a tear relative to the top side of the tear as defined by the underside of the planar surface.

Figure 3:
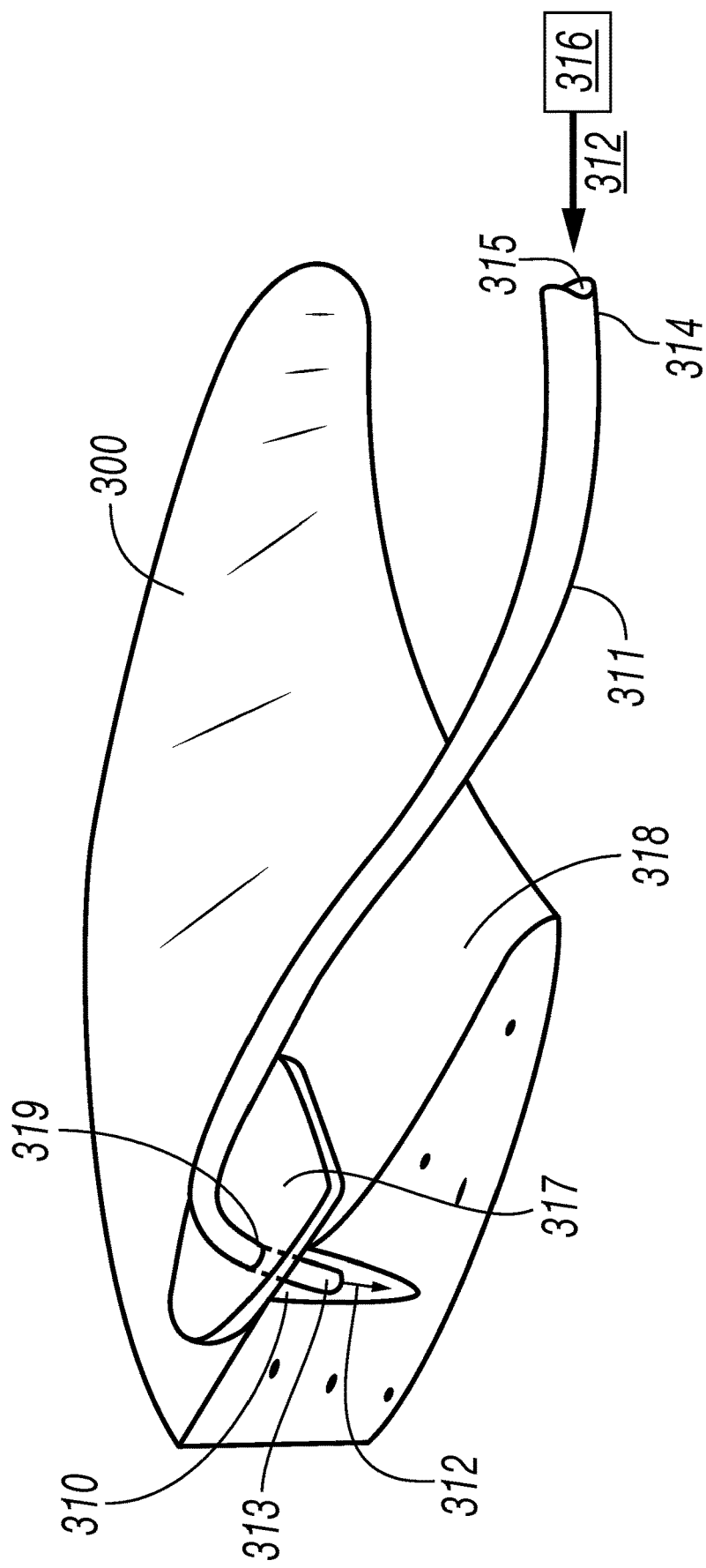
FIG. 3 is a perspective view showing an embodiment of the invention wherein a tubular component (e.g., cannulated probe) is capable of delivering an adhesive into a tissue tear, such as a meniscus tear, and wherein the device has a planar surface (e.g., stop) locatable on the superior meniscal surface above a tear to be repaired.

FIG. 3 is a perspective view showing an embodiment of the invention wherein a hollow or cannulated probe 311 is used to deliver (inject, administer, spray, or the like) at least one adhesive 312 from a source 316 of the one or more adhesive 312 into a tear 310 in a soft tissue 300, such as a tear in the medial meniscus.

The hollow or cannulated probe 311 is elongated and has a distal end 313 and a proximal end 314. The hollow or cannulated probe has at least one lumen 315. In some embodiments the one or more lumen(a) 315 extend(s) the length of the probe 311, from its proximal end 314 to its distal end 313. As discussed above for FIG. 2 (e.g., lumen 215), while multiple lumina within the probe (cannula) are not shown, they are understood to be within the scope of this disclosure, including that they may extend the length of a cannulated probe as does the lumen 315 shown in FIG. 3.

The source 316 of the one or more adhesive 312, and the adhesives 312 are discussed above for FIG. 2; all aspects disclosed in FIG. 2 at least for source 216 and adhesive 212 are applicable to FIG. 3, for example, source 316 and adhesive 312.

FIG. 3 also shows embodiments of the invention wherein a tubular component 311 is capable of delivering an adhesive 312 into a tear 310 in a soft tissue such as a meniscus 300, and wherein the device has a planar surface 317, attached, attachable (reversibly or irreversibly) to, and/or formed as part of an outer surface 319 of cannula 311. The location of attachment, attachability, and/or formation of the planar surface 317 on the outer surface 319 of cannula 311 may be a desired, defined location; for example, it may be located such that when the planar surface 317 lies flush with and/or flat with the superior meniscal surface 318 over and/or near the tear, the length of cannula 311 distal to the location of the planar surface is designed to allow the distal end of the cannula 313 to enter into the tear 310 to a desired depth for the administration (injection, spraying, or the like) of adhesive 312 into the tear 310 from the distal end of the cannula 313. In certain embodiments, the planar surface 318 may be located at 319 (attachable to, attached to, formed as part of, and the like) such that is acts as a depth stop; for example, allowing only a defined amount of the distal portion of the cannulated probe 311 (the portion of 311 extending distal from the location of the planar surface 317 on the cannula) to penetrate into, and thereby deliver adhesive 312 to a specific depth in the tear 310. In some embodiments of the invention, the planar surface 317 is reversibly attachable to the outer surface 319 of cannula 311 so that, for example, a manufacturer or a surgeon or other medical professional may attach and/or adjust the location of the planar surface 317 for a desired use of the planar surface 317 as a depth stop (e.g., allowing adjustability of the length (and/or depth) of the distal region of cannula 311 that may be introduced below the meniscal surface).

Figure 3A:
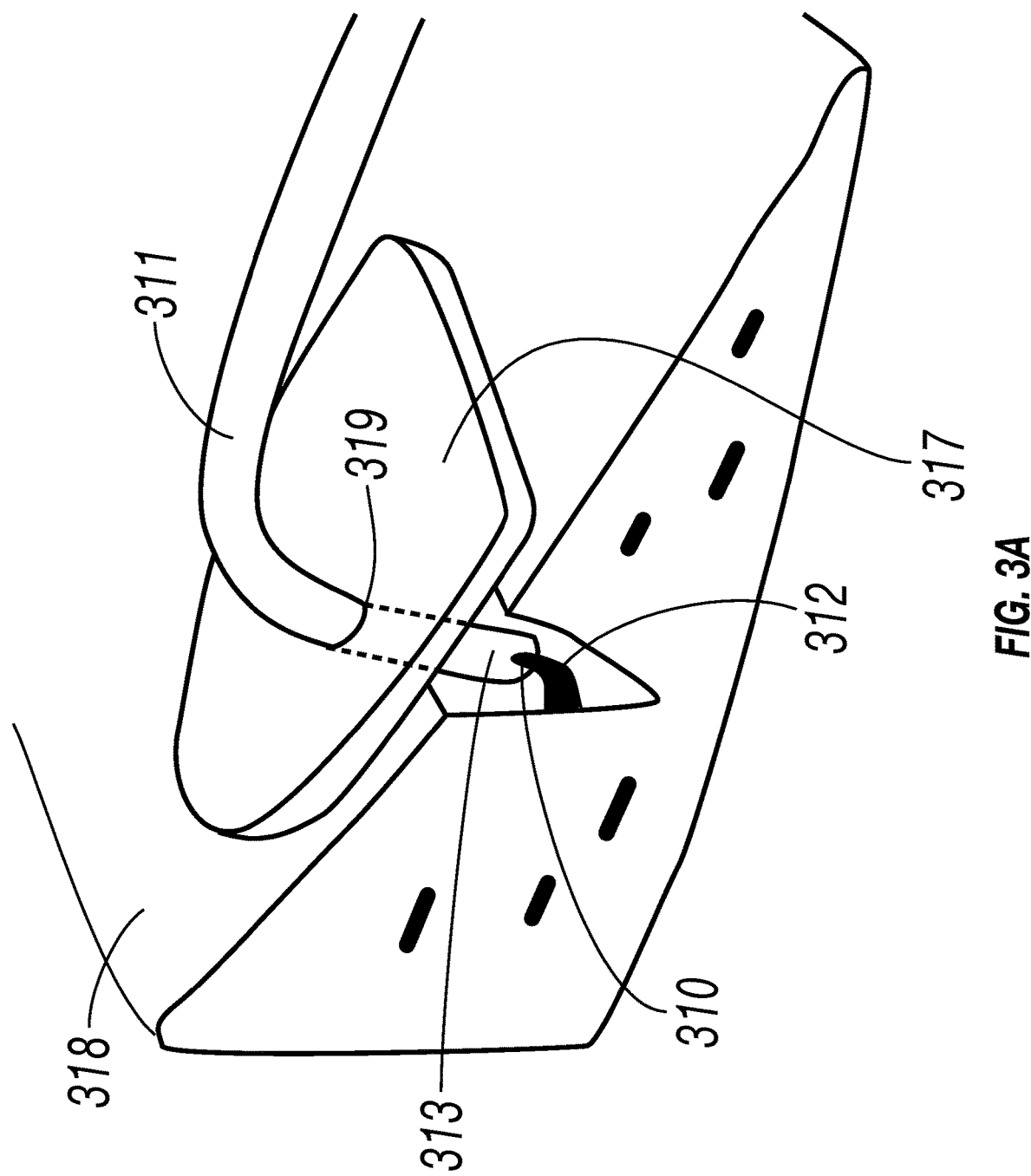
FIG. 3A is a partial view of FIG. 3 showing an enlarged perspective view of the planar surface of the device locatable on the superior meniscal surface above a tear to be repaired.

FIG. 3A is a partial view of FIG. 3 showing an enlarged perspective view of a distal region of the cannulated probe 311 and the planar surface 317 of the device locatable on the superior meniscal surface 318 above a meniscal tear 310 to be repaired.

Figure 4:
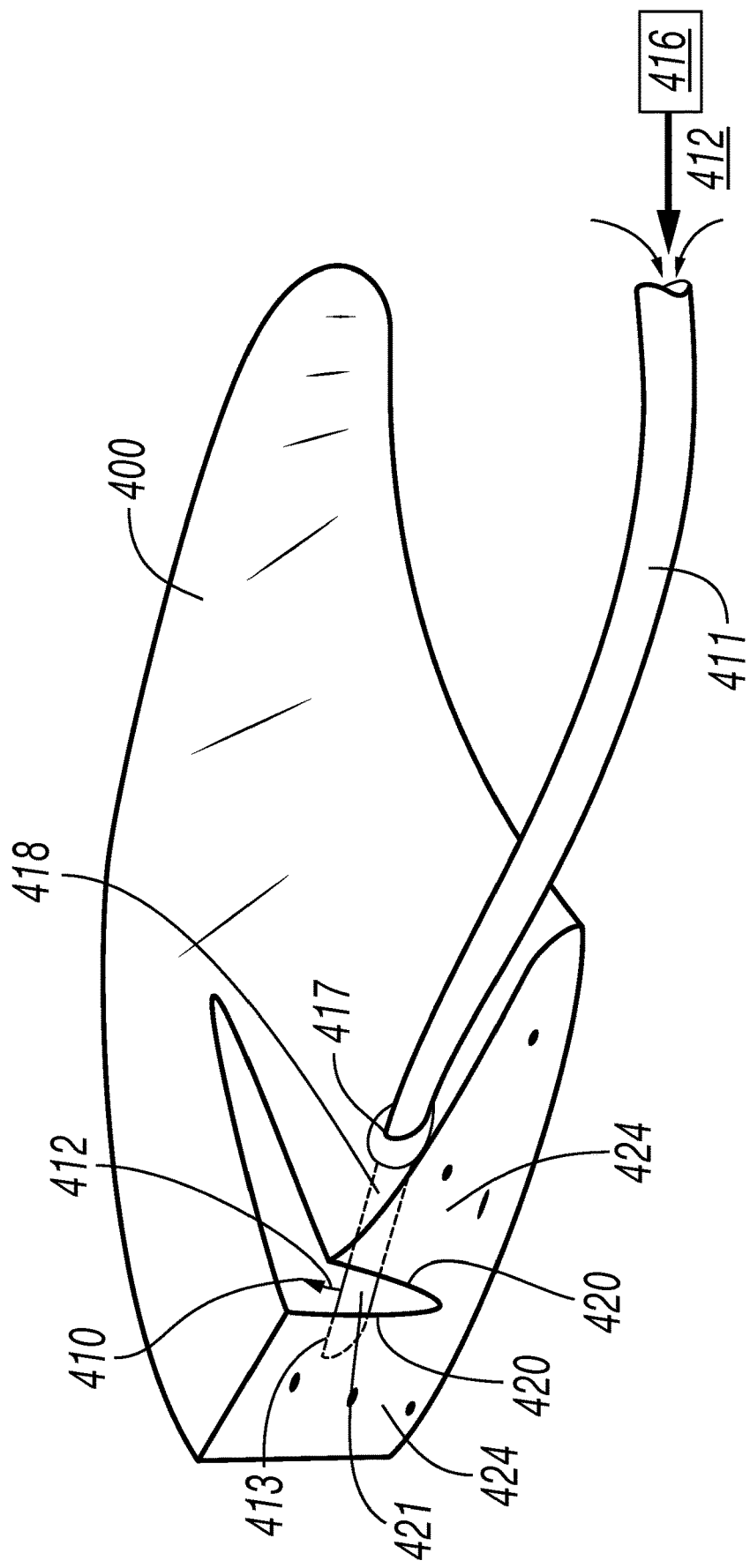
FIG. 4 is a perspective view showing an embodiment of the invention wherein a tubular component (e.g., cannulated probe) is capable of delivering an adhesive into a tissue tear, such as a meniscus tear, is inserted through a meniscus surface near the tear, and through both edges of the tear, to create a portion of the device that bridges the tear, wherein an adhesive is deliverable into the tear through side ports in the portion bridging the tear.

FIG. 4 is a perspective view showing an embodiment of the invention wherein a tubular component 411 is capable of delivering an adhesive 412 into a soft tissue tear 410, such as a tear in meniscus 400. FIG. 4 shows that needle 411 has been inserted through a meniscus surface 418 near the tear 410, the meniscus surface 418 and tissue immediately therearound and thereunder being healthy meniscal tissue. Further, the figure shows that tubular component 411 has been driven (e.g., by manual and/or automated manipulation) through meniscal tissue below surface 418 and the closest edge 420 of tear 410.

FIG. 4 further shows that the needle (tubular member) 411 has been inserted into tear 410 by its leading, distal end 413 exiting meniscal tissue near the closest edge 420 of tear 410. The figure also shows that cannulated, tubular component 411 is bridging the tear as the leading, distal end 413 of 411 has been inserted (not by limitation, but substantially perpendicularly) into the opposing wall 420 and into tissue 424 (including at least some healthy tissue) beyond and substantially behind the insertion point in the wall 420. The bridging of the tear 410 defines a region 421 of needle 411 which region bridges the tear.

Therefore, FIG. 4 shows, among other things, that the needle (cannula) 411 is inserted through a surface 418 (here, but not by limitation, a healthy surface with healthy tissue 424 underneath) near a tissue tear 410 (such as a torn meniscus; here as shown, but not by limitation in a direction substantially perpendicular to the lengthwise direction of the tear), entering the tear, bridging the tear 410 (the bridge defining region 421 of 411) and exiting the tear through the opposing surface 420, and into tissue 424 (at least some of which is healthy tissue).

Figure 4A:
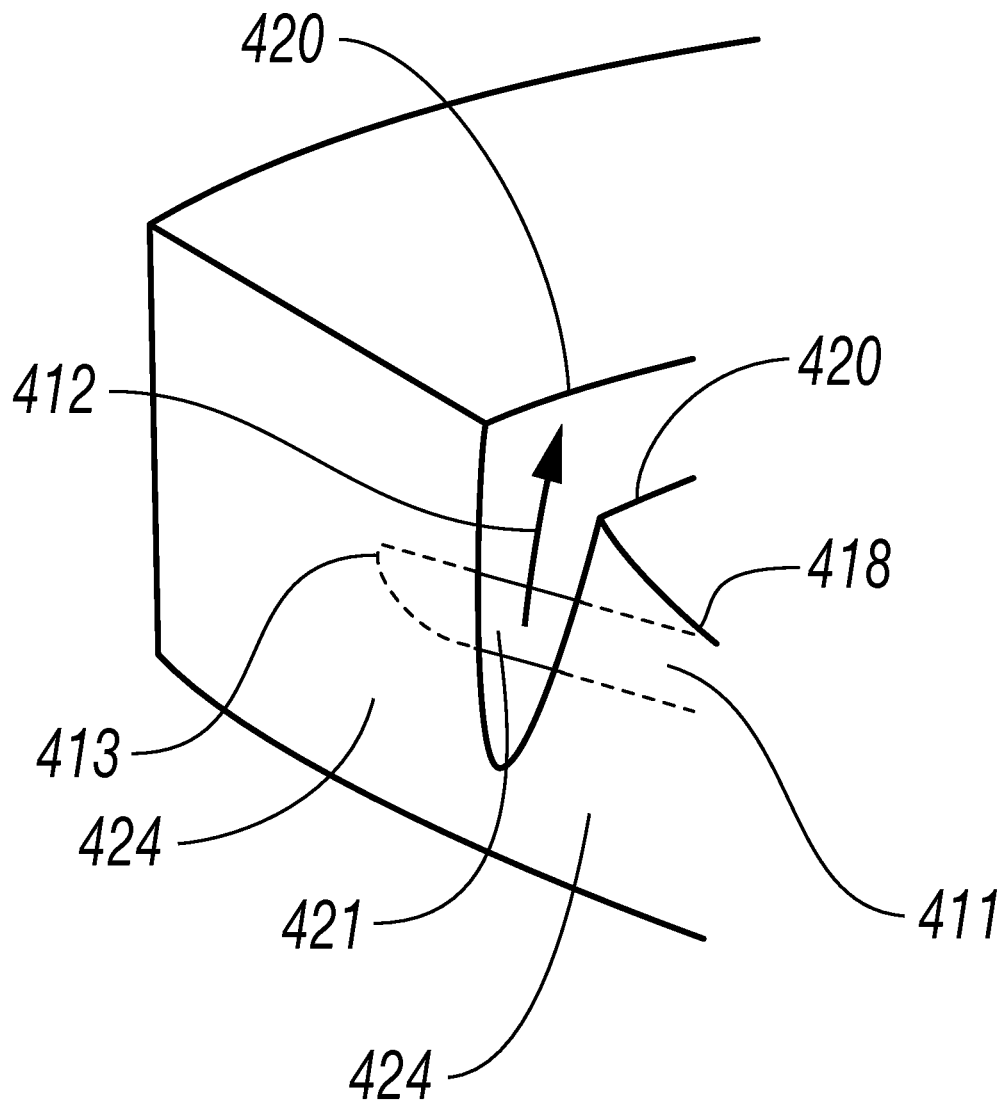
FIG. 4A is a partial view of FIG. 4 showing an enlarged perspective view of the device penetrating a meniscus surface near the tear, and through both edges of the tear, to create a portion of the device that bridges the tear, wherein an adhesive is deliverable into the tear through side ports in the portion bridging the tear.
Figure 4B:
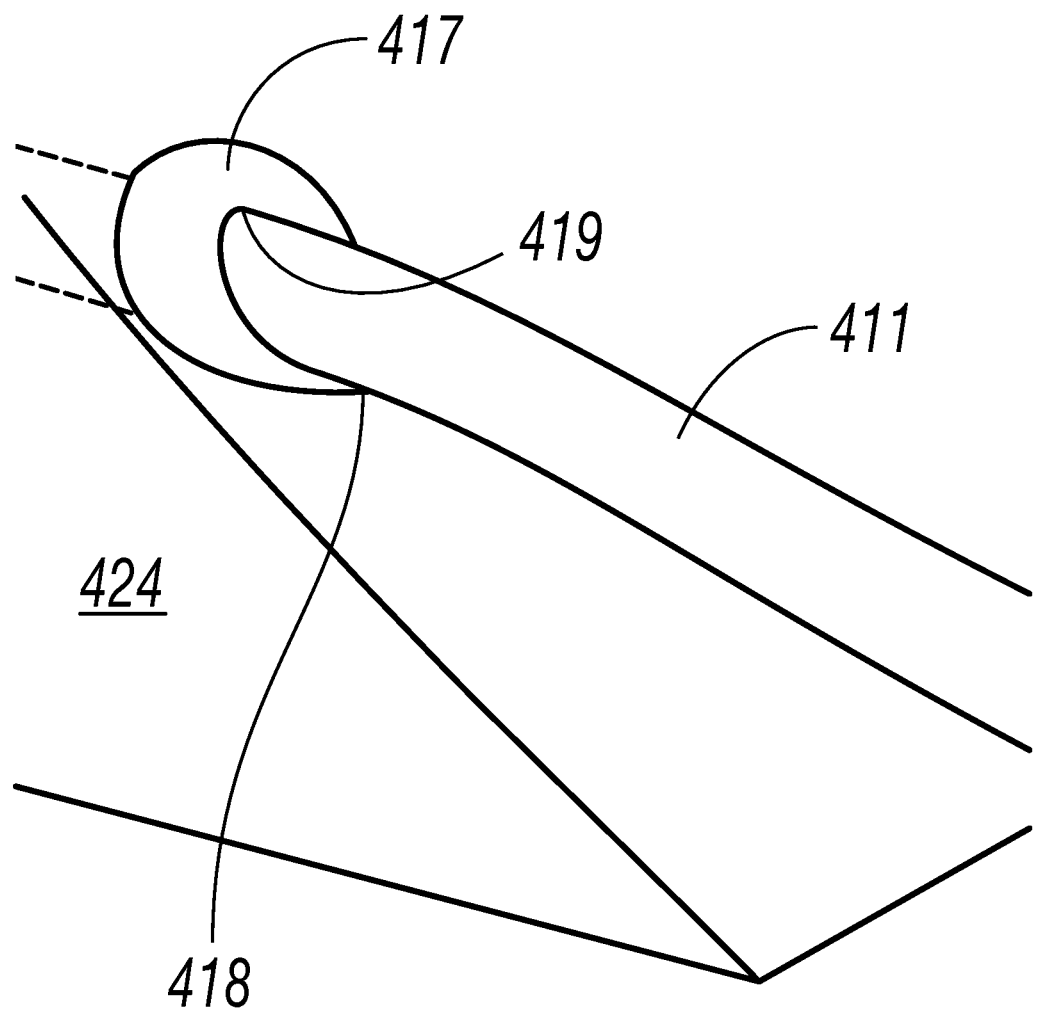
FIG. 4B is an enlarged perspective view of the depth stop of FIG. 4 located on the outer surface of the device and fitted so that when flush with the meniscal surface the device is properly positioned to bridge the tear and inject adhesive into the tear.
Figure 4C:
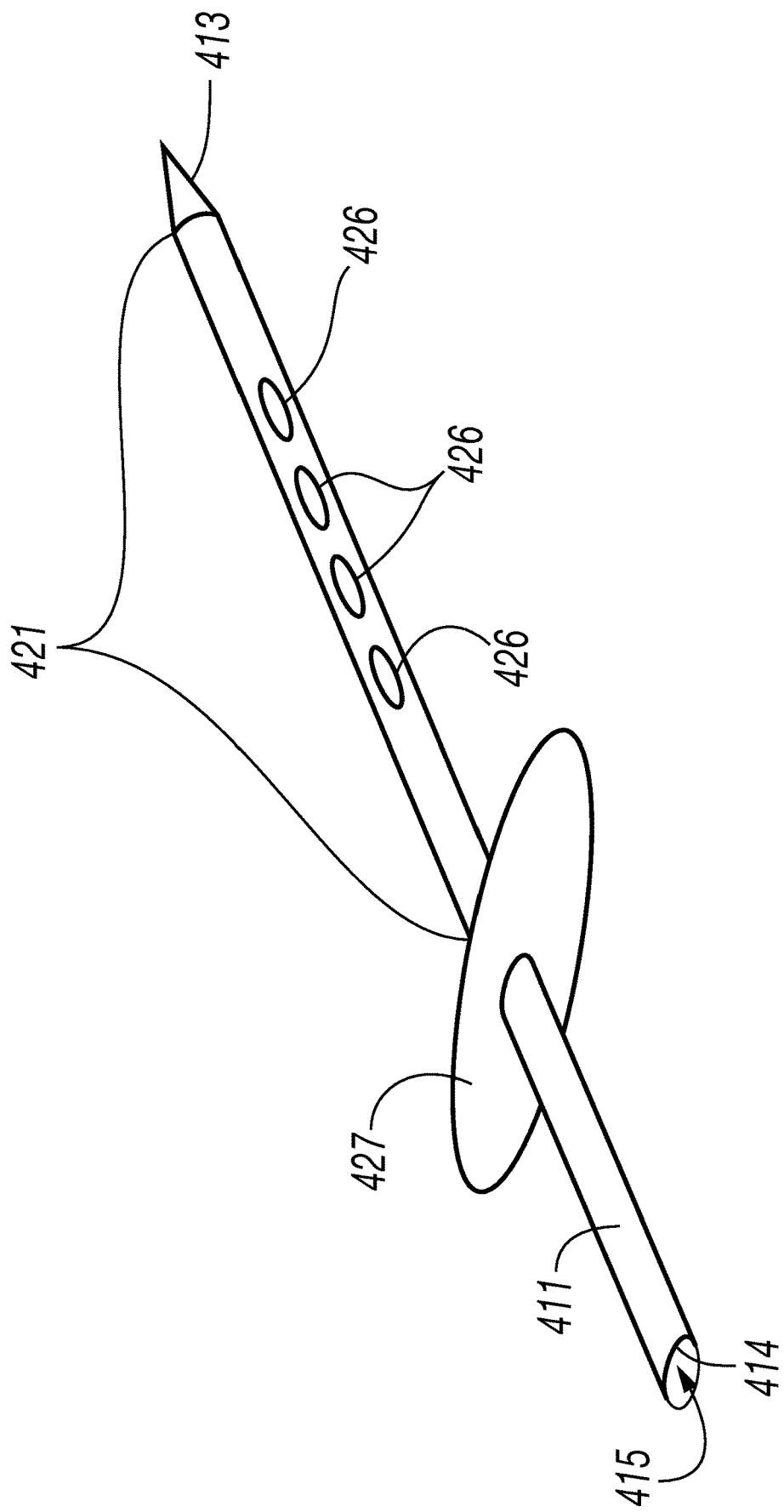
FIG. 4C is an enlarged perspective view of the distal end of the device of FIG. 4, showing side ports within a region of the device designed to span a meniscal tear when inserted to administer an adhesive into the meniscal tear.

While not by limitation, it is believed that (as shown in FIGS. 4, 4A, and 4C) tubular component 411 lodged within tissue 424 (wherein it is understood that tissue 424 includes (but not by limitation) tissues at or near the edges and bottom of the tear, deeper than (or further from) the edges and bottom of the tear, and pathologic and non-pathologic tissues)) may, for example, assist with anchoring, stabilizing, and/or controlling the position and/or location, and/or depth of 411 (and subsequently bridging region 421, including location and/or direction of the side ports for adhesive injection in 421 (see FIG. 4C)).

Further, and not by limitation, it is believed that the above described stabilization, localization, and/or depth definition of tubular component 411 bridging the tear 410 (i.e., portion 421 of 411 needle (see FIG. 4C)) may also assist in localizing, and defining, and in some embodiments confining, the area in which adhesives are delivered into the tear and/or surrounding tissue by the tubular component (needle). For example, as shown in, but not by limitation by, FIG. 4C (discussed below), the needle (tubular member) 411 once properly placed to bridge the tear may inject adhesive only by the side ports in region 421 and, therefore, only into the tear and not for example into the surrounding (e.g., healthy) tissues 424; it may also inject adhesive into tissues 424, alone or with injection through side ports (not shown in FIG. 4) in region 421. Aspects of this embodiment may be of particular importance where an adhesive and/or components of an adhesive mixture may be toxic or potentially toxic to surrounding tissue. In such cases, embodiments wherein the needle 411 administers adhesive(s) only by side ports in 421 and does not administer adhesive 412 beyond the side ports in the region 421 (e.g., does not administer an adhesive mixture via side ports or the like proximal to those within region 421 when properly positioned in the tear, and does not administer an adhesive mixture from any region distal to region 421, are desirable; for example, for maintaining tissue integrity (such as healthy tissue integrity) in tissue 424. In such embodiments (and in others), the side ports in region 421 may be angled toward the center of the tear in order to further assure that an adhesive mixture is administered only within a tissue tear and not into surrounding tissue.

Furthermore, as discussed in more detail below and shown in FIG. 4B, in such embodiments the use of a depth stop 417 may be useful (and, while not necessary for all embodiments, may be especially useful (but not necessarily required) to the needle-bridging embodiments shown and discussed for example with regard to FIG. 4 (and FIGS. 4A-C) in assisting that when fully inserted the needle 411 is located such that the side ports in region 421 line up with only the opening within the tear and would not, for example, administer adhesive into tissue surrounding the tear edges 420.

To further assist with anchoring, stabilizing, and/or localizing (for example in defining the depth of insertion, the orientation of tubular component 411 and its region 421 within in the tear of region) the tubular component 411 may be inserted directionally with regard to the length of a tear, for example, such that when bridging the tear the direction of tubular component 411 (and subsequently region 421) is substantially perpendicular to the lengthwise direction of the tear 410. This is illustrated, for example, in FIGS. 4-4C. However, this is not required and the needle 411 may be inserted and bridge tear 410 at substantially any orientation such that it is capable of delivering adhesive within the tear and preferable of stabilizing the needle 411 when inserted to bridge the tear.

In certain embodiments of the invention, the needle 411 may be reversibly inserted to bridge tear 410 (reversibility not explicitly shown in the figures). For example, in such cases, the insertion and bridging may be useful for directing application of adhesive to a desired location within a tear. After the application of any desired amount of adhesive to the tear, the needle may be withdrawn, for example, completely from the subject tissue (e.g., a meniscus). In some embodiments, the needle is removable, but may be withdrawn after a certain amount of time and/or when other conditions are met, for example, for assuring that the needle is not removed until the adhesive has had time to develop certain properties (e.g., strength on its own; e.g., without a need for the needle to assist in stabilizing adhesion) before needle 411 is removed.

In certain embodiments of the invention, various embodiments of the adhesive injection device, system, and method, may include withdrawing adhesive and/or byproducts of in situ adhesive formation through the same, or substantially the same devices discussed herein. The withdrawing of adhesive(s) (adhesive mixtures, and the like) may be desirable in situations wherein, by non-limiting example, an adhesive mixture contracts and increases in density in situ, leaving excess liquid. Removing such excess liquid using the cement injection technology disclosed herein can be desirable in such instances. Embodiments disclosed herein may also be used for removing excess fluids of any type (such as those associated with inflammation) regions within a body, such as hard to reach regions and anatomy, such as joints, including knee joints.

Still further, in certain embodiments of the invention, an elongated tubular member (e.g., but not limited to 211 shown in FIG. 2) with one or more lumen(a) (e.g., but not limited to 215 shown in FIG. 2) may be temperature controlled. For non-limiting example, an adhesive injection device such as 211 shown in FIG. 2 may further contain a heater (not shown), such as, but not limited to, a heating element (not shown) located within the one of more lumen (a) 215 and/or associated with the hollow, cannulated probe 211 (e.g., externally (not shown)). This provides, for example, an ability to inject temperature sensitive adhesive(s) and mixtures. This includes, for example, the ability to inject adhesive(s) into a body where the adhesive(s) may have poor (to no) flowability properties at temperatures below about 37° C. (e.g., due to solid state, high viscosity, and/or stickiness to the walls of the lumen(a)). In such cases, the adhesive(s) to be injected may be heated to about 37° C. before being loaded into the proximal end of the at least one lumen(a) 215 (which might, but not necessarily is, a separate lumen from a lumen containing a hearing element) and thus be kept at 37° C. during the time it takes to inject the adhesive(s) into the desired in vivo location. In certain embodiments, the temperature of the needle, or portions of the needle may exceed 37° C. so long as tissue at the site of application is not injured or killed by the temperature of the applied adhesive. Embodiments may also have a cooler (not shown) within or associated with a tubular, cannulated probe (e.g., 211 of FIG. 2). Such embodiments may be especially useful for administering adhesive(s) that are suitably flowable at or below room temperature and that take on superior adhesion properties when their temperature is increased to about 37° C.

FIG. 4A is a partial view of FIG. 4 showing an enlarged perspective view of a cannulated device 411 of an embodiment of the invention penetrating a meniscus surface 418 near the tear 410, and through both edges 420 of the tear, to create a portion 421 of the device that bridges the tear. FIG.

4A further shows an adhesive 412 being delivered into tear 410 through side ports (not shown in FIG. 4A, see FIG. 4C) located in region 421 of cannulated device 411. Because the side ports are located between the edges of the tear 420, the adhesive(s) is injected into the tear 410. In certain embodiments, such as that shown in FIG. 4A, adhesive 412 is only delivered (administered, sprayed, injected, and the like) into the tear 410 via side ports in region 421 and not into tissue 424 (discussed, e.g., above for FIG. 4) which contain at least some non-pathologic tissue in which sections of the cannula 411 proximal and distal to region 421 are lodged at least while adhesive(s) is applied to the tear.

FIG. 4B shows an enlarged perspective of the optional depth stop 417 shown in FIG. 4 and discussed above. The depth stop 417 is attached, attachable (e.g., but not limited to adjustably or non-adjustably, reversibly, or irreversibly attached or attachable) to, and/or formed as part of an outer surface 419 of cannula 411. The location of the adjustable, non-adjustable, reversible, or irreversible attachability or attachment of depth stop 417 to cannulated member 411, and/or the formation of depth stop 417 as part of an outer surface 419 of cannulated needle 411 may be a desired, defined location; for example, it may be located such that when the depth stop 417 lies against (e.g., but not necessarily, flush with and/or flat with; i.e., such that depth stop 417 prevents further insertion of needle 411 into the tissue (e.g., a meniscus 400) having the tear, at tissue region 418).

The location of the depth stop 417 may be designed so that when the cannulated probe 411 is inserted through tissue region 418 (e.g., a superior meniscal surface) over and/or near the tear, the length of cannula 411 distal to the location of the planar surface is made to allow the distal end 413 of the cannula 411 to pass through tissue 424 (see FIGS. 4 and 4A) enter into the tear 410, through tear edge 420 (see FIGS. 4 and 4A) closest to advancing needle 411 to a desired depth for the distal end of needle 411 to pass through the opposing tear edge 420 (see FIGS. 4 and 4A) and back into tissue 424 to allow region 421 of needle 411 to bridge the tear 410 (as shown and described above including e.g., in FIGS. 4 and 4A).

FIG. 4C is an enlarged perspective view of the distal end of the cannulated needle device 411 of FIG. 4, showing side ports 426 within the region 421 of the needle 411 designed to span a tissue tear 410 (such as, e.g., a tear in a meniscus (not shown in FIG. 4C)). FIG. 4C also shows a depth stop 417, similar to those in FIGS. 4 and 4C and designed to have the substantially or the same function (e.g., but not limited to, defining the depth of the insertion of needle 411 into tissue so that when fully inserted the region 421 of needle 411 bridges the tear and is aligned over the tear such that, e.g., when adhesive is delivered through side ports 426 is it delivered into the tear (and not into the surrounding tissue 424 (shown, e.g., in FIGS. 4-4B). FIG. 4C also shows, for example, distal 413 and proximal 414 ends of cannulated needle 411. As with the embodiments shown and described above, the proximal portion of cannula 411 extends beyond the depth stop 417 to a point where adhesive(s) and/or adhesive mixtures are loaded (injected and the like) into at least one lumen(a) 415 of the cannula 411.

In embodiments wherein a single lumen is used to inject adhesive, the side ports 426 may be in direct communication with the lumen, allowing for direct injection of the contents of the lumen into the tear. In embodiments wherein more than one lumen is used to carry adhesive(s) and/or other injectable components to the injection site for delivery in vivo, the cannula may have the two or more lumina merge into a single lumen prior to reaching side ports 426, or certain side ports may be associated with certain lumina for directly applying separate components for mixing in situ. Other styles of delivery are known and knowable in the art.

Figure 4D:
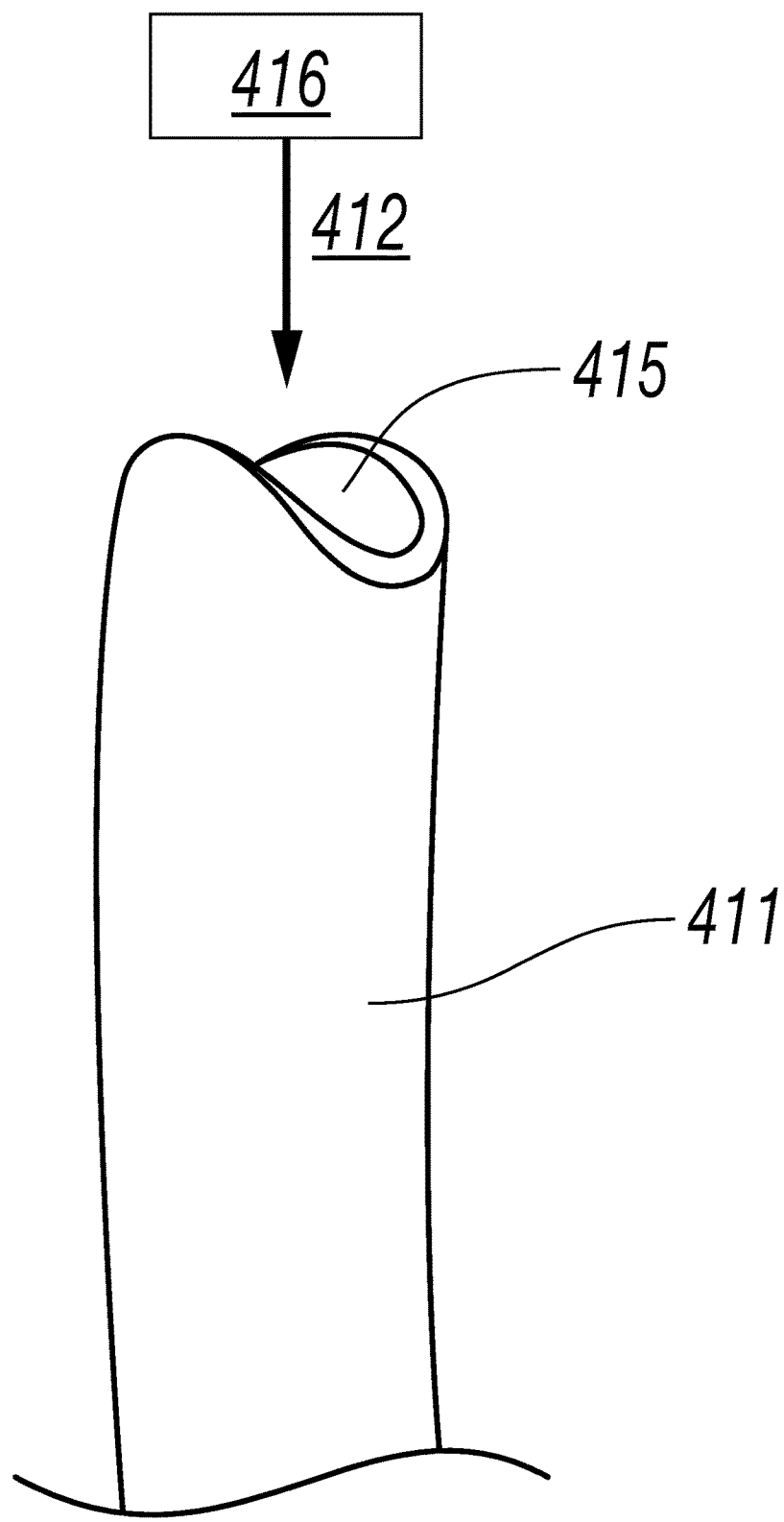
FIG. 4D shows a perspective view of the proximal end of the device of FIG. 4, showing an adhesive capable of being administered therein.

FIG. 4D shows a perspective view of the proximal end 414 of the cannulated device 411 of FIG. 4, showing a source 416 of the one or more adhesive 412 and the at least one lumen(a) 415.

Figure 5:
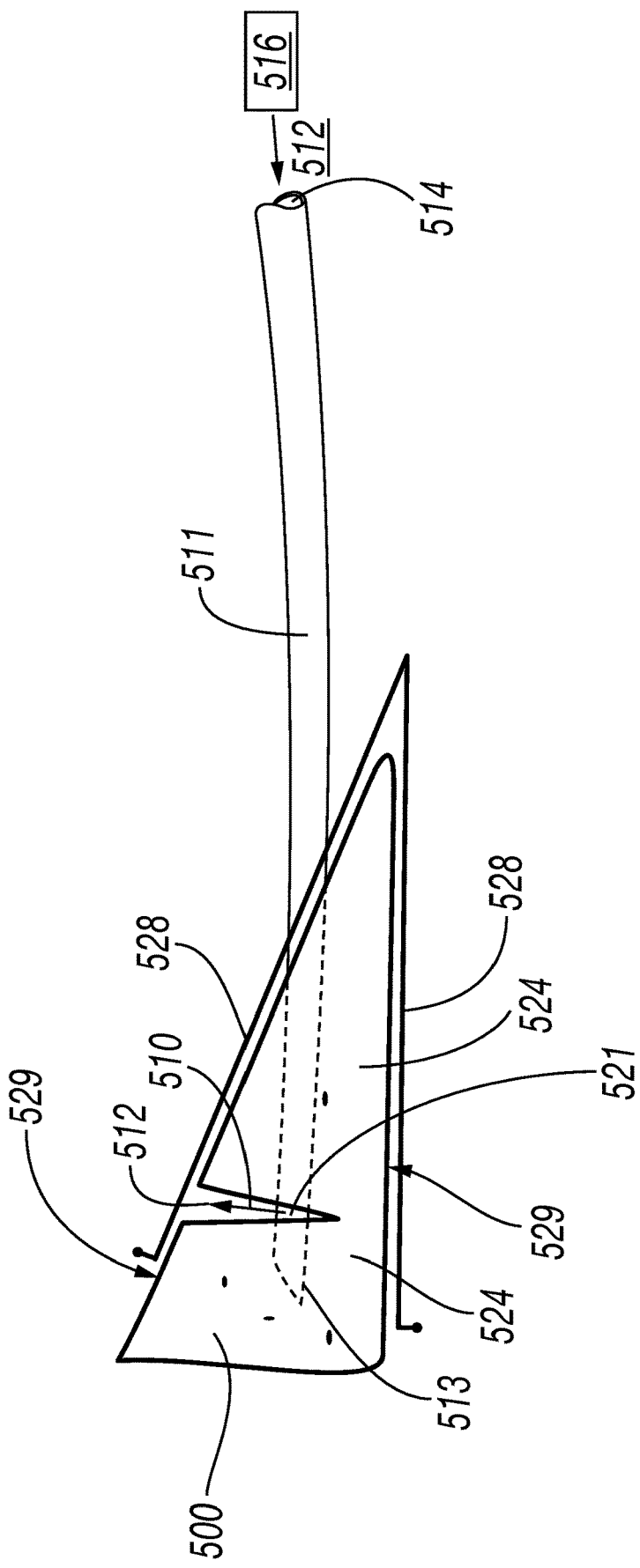
FIG. 5 is a perspective view showing an embodiment of the invention wherein a fixed or adjustable v-shaped clip is capable of securing each planar side (for example, femoral and tibial) of a meniscus while an injection mechanism (e.g., cannulated probe) deposits adhesive into a tear region contained between the planar surfaces.

FIG. 5 is a perspective view showing an embodiment of the invention wherein a fixed or adjustable (e.g., bendable) clip 528, such as a v-shaped clip as shown, is capable of and/or is used for securing two opposing planar sides 529 of a tissue, such as a meniscus 500, having at least a tear 510 in one of the opposing sides. This includes, but is not limited to, a tissue such as a meniscus 500, having a femoral and/or a tibial tear.

The figure also shows an embodiment similar to those described above for FIGS. 4-4D wherein a cannulated device 511 is inserted through a surface of substantially healthy tissue near the tear and into such tissue 524, passing through the tear 510 and exiting the tear into a region of substantially health tissue 525. This includes defining a region 521 of needle 511 which region bridges the tear. As shown in more detail in FIG. 4C, in such embodiments, adhesives 512 may be injected into the bridged tear through side ports (not shown in FIG. 5) on the cannula 411 in region 421.

In non-limiting examples of embodiments related to FIG. 5, the clip 528 may be made of non-bendable material, for example, supplied in different sizes designed to provide an appropriately tight fit over the subject tissue. The clip 528 may also be made of a semi-rigid, minimally bendable material that allows some degree of bending and holds a bent position. In these embodiments, the clip 528 may be placed over the appropriate locations on the tissue and then bent (e.g., by hand pressure) to a degree of firmness of clamping that is appropriate for the particular clinical setting. Bendable clips may also be provided in a series of sizes so that a health professional may initially choose a size that is close to the desired final, bent size. Appropriate materials include but are not limited to all biocompatible materials known or knowable in the art exhibiting the above described properties. These may include, but are not limited to, clips made of plastics (plastic bends, etc.) and metals, including those having shape memory properties.

While not necessary, the bendable clip may also be bendable in an opening manner, such that after achieving the benefits of use of the chip in a firmly bent position, a more open clip may help avoid damaging healthy and/or healing tissue, such as avoiding reopening a tear and/or creating new tears in or abrasions on the healthy surface of surrounding tissue.

FIG. 5 also shows the proximal end 514 of the cannulated device 511, showing a source 516 of the one or more adhesive 512 and the at least one lumen(a) 515.

Figure 6:
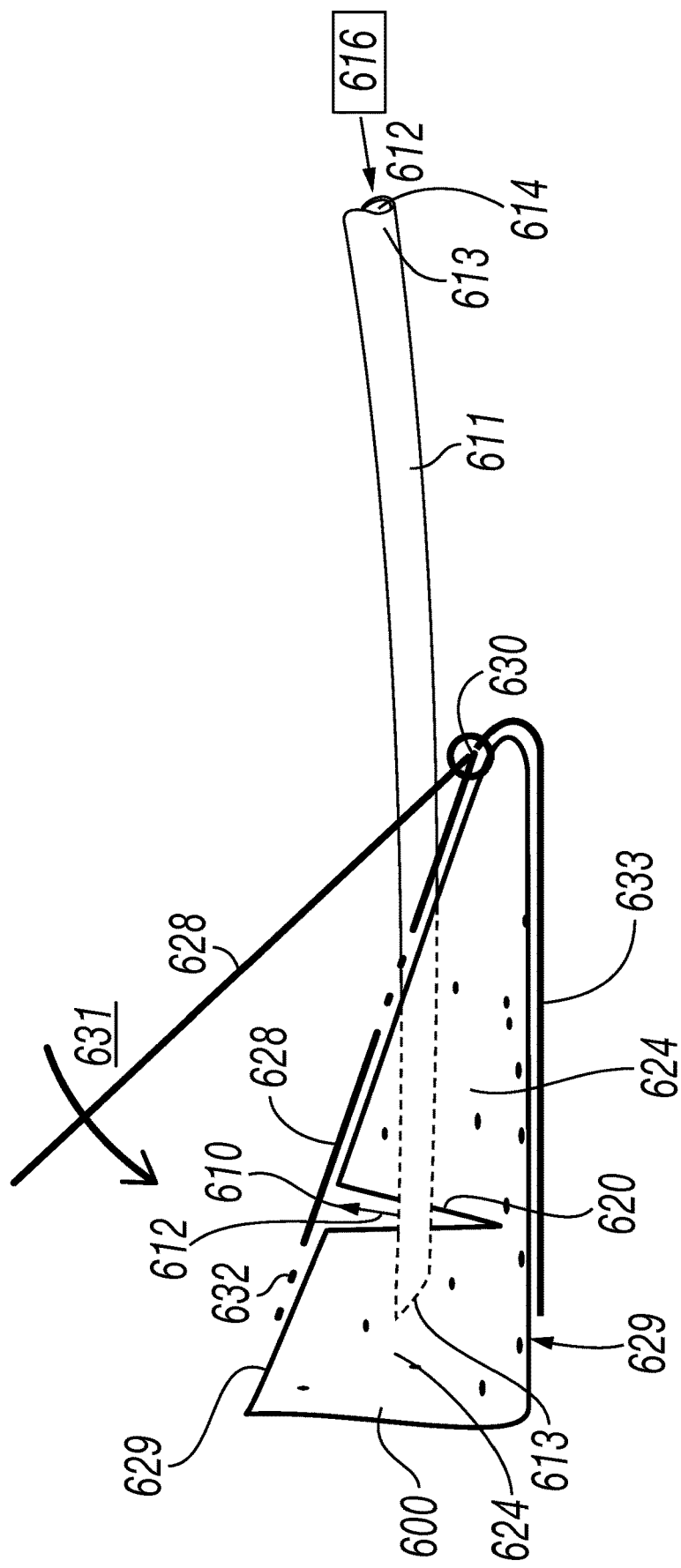
FIG. 6 is a perspective view showing an embodiment of the invention wherein adjustable hinged shaped plates are capable of securing each planar side (for example, femoral and tibial) of a meniscus while an injection mechanism (e.g., cannulated probe) deposits adhesive into a tear region contained between the planar surfaces.

FIG. 6 is a perspective view showing an embodiment of the invention wherein adjustable hinged plate 628 and lower plate 633 are capable of and/or are used for securing two opposing planar sides 629 of a tissue having at least a tear in one of the opposing sides 629. This includes, but is not limited to, a tissue such as a meniscus 600, having a femoral and/or a tibial tear.

FIG. 6 also shows an embodiment wherein a cannulated probe 611 does not bridge the tear 610 (and, accordingly, the cannulated probe 611 does not have a tear bridging region similar to 421 and 521 as shown and discussed above). Rather, in the embodiment of FIG. 6 the cannulated probe 611 is inserted through a surface of and into substantially healthy tissue 624 near the tear, then passed through the tissue 624 until the proximal end 613 of the probe 611 penetrates the edge 620 of tear 610. Adhesive is then delivered into the tear from an opening (not shown) at or near the distal end 613 of cannulated probe 611.

In non-limiting examples of embodiments related to and as shown in FIG. 6, the adjustable hinged plate 628 and the lower plate 633 are adjustable between each other via a hinge 630 which connects the two. For example, FIG. 6 shows that the angle of hinged plate 628 to lower plate 633, via hinge 630, may have at least two arrangements relative to each other, open and closed. In the open position, hinged plate 628 is at position 631 relative to the lower plate 633 and the hinge 630. In the closed position, hinged plate 628 is at position 632 relative to the lower plate 633 and the hinge 630. Therefore, when in the open position (hinged plate 628 at position 631), the angle (and size of opening) between hinged plate 628 (at position 631) and lower plate 633 is greater than the angle (and size of opening) between hinged plate 628 (at position 632) and lower plate 633 when the plates are in the closed position.

Without limitation, in some embodiments of the invention, the two or more angles of the hinged plates to one another allow a medical provided to adjustably fit the plates appropriately over the tissue to be bound, and then increase that pressure. For example, as shown in FIG. 6, when the plates are in the open position and the angle between the two is wider than the angle in the closed position, the hinged plates may be appropriately fitted over tissue to be held between the closed plates. One so fitted, an operator may move the adjustable hinge plate 628 from open position 631 to closed position 632, where, in the closed position, the plates hold the two opposing sides of tissue more firmly (with more pressure applied, and the like) than would be the case in the open position.

The ability to switch from the or an open position to the or a more closed position may be one-way or reversible, and controlled by or related to any technology known or knowable in the art. For example, the hinged component may be provided in a fully open configuration, and the hinge may be such that compression on the hinged plate toward the lower plate irreversibly moves the hinge to the, or a, closed position. In such instances, once compressed to a desired position, the hinge holds the position firmly. In other embodiments, the hinge may be reversible, yet also be capable of holding one or more closed positions until specifically opened by, for example, an medical provider (with or without the assistance of a particular device). In the latter, the hinged plates may be held in a closed position for a time necessary for the adhesive to fully adhere the tear and/or for the tear to heal naturally (including as assisted by the adhesive). When the hinged device is no longer necessary, a medical professional may then disengage or otherwise release the hold of the hinge, allowing the plates to return to a more or fully opened condition. The opened plates may then be removed from the tissue. While not necessary, removing the plates when they are more open may help avoid damaging healthy and/or healing tissue, such as avoiding reopening the tear and/or creating new tears in or abrasions on the healthy surface of surrounding tissue.

In non-limiting examples of embodiments related to FIG. 6, appropriate materials for the plates and hinge include all biocompatible materials known or knowable in the art exhibiting the above described properties. These may include, but are not limited to, plates and hinges made of plastics (plastic blends, etc.) and metals, including those having shape memory properties.

FIG. 6 also shows a perspective view of the proximal end 613 of the cannulated device 611, showing a source 616 of the one or more adhesive 612 and the at least one lumen(a) 614.

Figure 7:
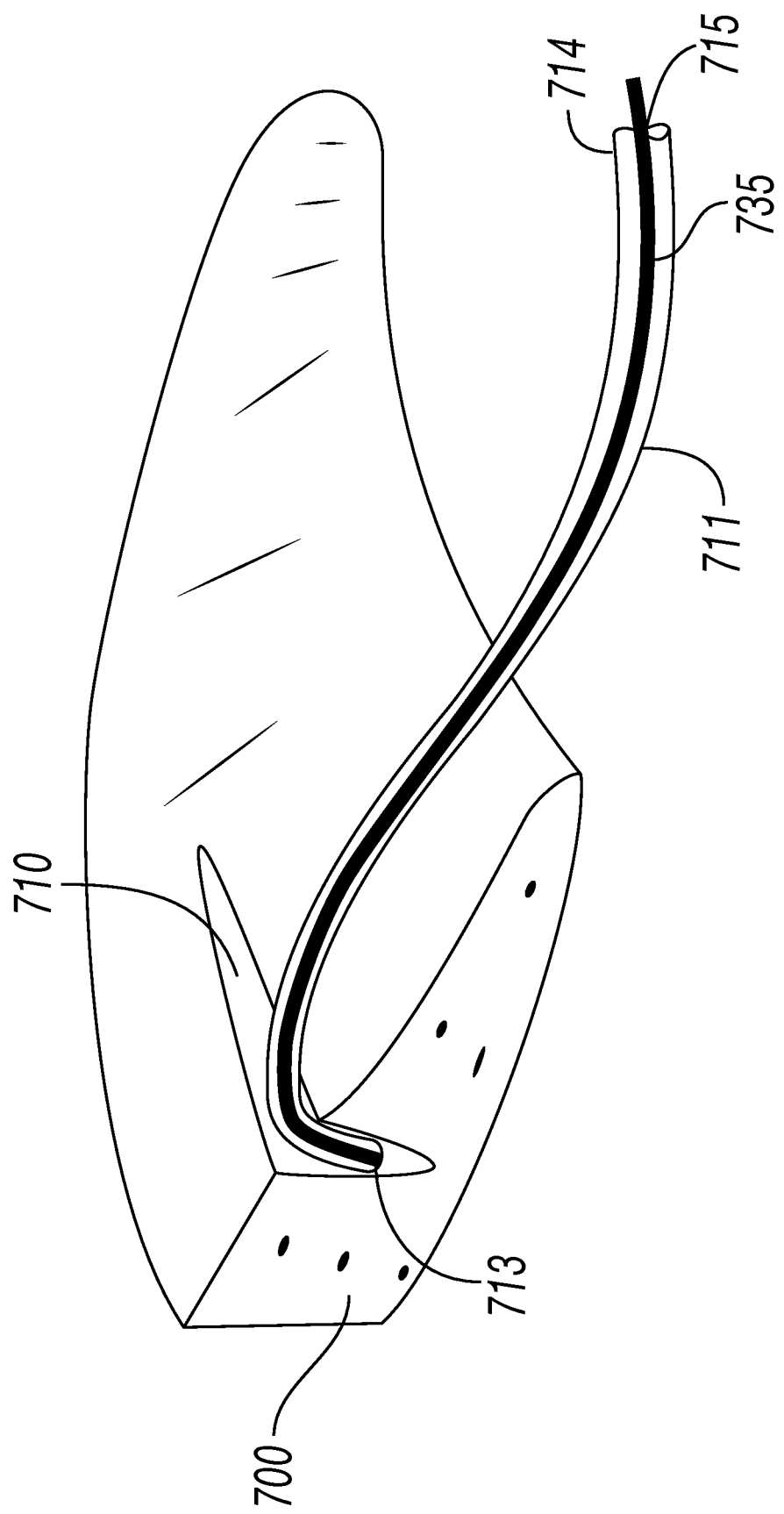
FIG. 7 is a perspective view showing an embodiment of the invention wherein an optical fiber is disposed within an adhesive delivery system (e.g., cannulated probe), for example, in the application of an adhesive to a meniscal tear.

FIG. 7 is a perspective view showing an embodiment of the invention wherein an optical fiber is disposed within an adhesive delivery system, for example, in the application of an adhesive to a meniscal tear. Specifically, FIG. 7 shows a section of tissue, such as a meniscus 700 having a tear, such as a meniscal tear 710. The figure further shows a hollow cannulated structure 711, having a distal end 713 and a proximal end 714. FIG. 7 shows the hollow cannulated structure as having one lumen 715 that runs from the proximal end 714 to the distal end 713 of the cannula 711. However, it is to be understood that the cannula 711 may have two or more lumina, that may run the full length of the device 711 and/or wherein some or all lumina may, for example (but not shown) merge into a common lumen near the distal end 713 of cannula 711.

FIG. 7 also shows an optical fiber 735. As shown, the optical fiber 735 runs the length of the hollow cannula (cannulated needle, multi-lumina cannula, etc.), from the proximal end 714 to the distal end 713. As shown in FIG. 7, the optical fiber 735 is disposed within the lumen 715. For non-limiting example, the optic fiber 735 may be disposed within a separate lumen of a multi-lumina cannula. The optic fiber 735 may also be associated with the cannula 711, such as but not limited to, by being attached to the cannula 711. An object of the optical fiber is to provide visualization to a medical professional of the area proximate to the distal end of cannula 711. The fiber may also and/or alternatively be used to provide a source of energy to adhesive applied in situ, such as in the initiation of polymerization of a polymer adhesive. More than one optical fiber may also be used; for example, one fiber may provide the above-described visualization and another as the above-described source of energy for crosslinking and/or polymerizing an adhesive in situ (and/or the same fiber may be used for both purposes). Any biologically compatible optical fiber(s) (or fiber optic(s)) (including but not limited to fiber optic (optical fiber) systems) known or knowable may be suitable for use as described and shown herein.

In embodiment of the invention, the cannula (probe, needle, and like terms) can be made of any biologically compatible material(s) known or knowable in the art. In embodiments, the cannula may be rigid, semi-rigid, or flexible.

In some embodiments, the cannula may have more than one lumen. In some embodiments of multi-lumen cannulae, at least one lumen may be used for driving the insertion, direction, placement, and optional removal of the cannula from tissue. For example, a lumen, such as a blind lumen, in a cannula may receive a guide wire which may be used to direct the insertion (location, direction, depth, etc.) of a cannula. The guide wire may extend beyond the proximal end of the cannula, for example allowing for manual and/or mechanical maneuvering of the cannula.

FIG. 8 is a flow chart depicting a method 800 of repairing soft tissue. The method involves 840—providing having an inlet at a proximal end and at least one outlet about a distal end with a lumen therethrough, 842—disposing a stop about a periphery of the probe a distance from the inlet, 844—positioning a cannulated probe about a tear in the soft tissue, 846—terminating advancement of the cannulated probe about the soft tissue by positioning the stop adjacent a surface of the soft tissue, and 848—delivering the adhesive about the tear by passing an adhesive from the inlet, through the lumen, and out the at least one outlet.

The positioning 844 may involve inserting a tip of the cannulated probe into the tear, passing the cannulated probe through the tear by inserting a tip of the cannulated probe through the soft tissue on either side of the tear, and/or bridging the tear by extending the cannulated probe through soft tissue on either side of the tear. The method 800 may also involve 850—passing the adhesive out a plurality of the at least one outlets and into the tear, sealing the tear with the stop during the positioning, 854—disposing a fiber optic through the cannulated probe and visualizing the soft tissue, 856—clipping the soft tissue and disposing the cannulated probe through the clipped soft tissue, and/or 858—retracting the cannulated probe from the soft tissue.

Portions of the method may be performed in various orders, and repeated as desired.

While the embodiments are described with reference to various implementations and exploitations, it will be understood that these embodiments are illustrative and that the scope of the inventive subject matter is not limited to them. Many variations, modifications, additions and improvements are possible. For example, one or more features provided may be combined.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

Insofar as the description above and the accompanying drawings disclose any additional subject matter that is not within the scope of the claim(s) herein, the inventions are not dedicated to the public and the right to file one or more applications to claim such additional invention is reserved. Although a very narrow claim may be presented herein, it should be recognized the scope of this invention is much broader than presented by the claim(s). Broader claims may be submitted in an application that claims the benefit of priority from this application.

What is claimed is:

1. A medical device for repairing soft tissue, comprising:
   a cannulated probe formed from a single tubular wall defining a periphery of the cannulated probe and a single lumen therethrough, the cannulated probe positionable about a tear in the soft tissue, the single tubular wall of the cannulated probe forming a needle configured to penetrate tissue at a distal end, the single tubular wall having an inlet at a proximal end and at least one outlet about the distal end with the single lumen therethrough, the inlet connected to an adhesive source to receive an adhesive therein and deliver the adhesive through the single lumen to the at least one outlet, the at least one outlet positionable about the tear to emit the adhesive about the tear;
   a stop adjustably disposed about a periphery of the single tubular wall of the cannulated probe a distance from the inlet, the stop terminating advancement of the cannulated probe into the soft tissue and preventing further insertion when a delivery portion of the cannulated probe is positioned about the soft tissue to deliver the adhesive about the tear; and
   a v-shaped clip comprising an upper plate and a lower plate hingedly connected to the upper plate to define an opening to receive the soft tissue therein and grasp the soft tissue therebetween, wherein the upper plate is configured to fit over a planar surface of the soft tissue having the tear and the lower plate is configured to fit over an opposing planar surface of the soft tissue opposite the tear to secure the opposing planar sides of the tissue, the cannulated probe disposable through the v-shaped clip,
   wherein the single lumen extends the length of the single tubular wall of the cannulated probe between the inlet and the outlet.

2. The medical device of claim 1, wherein the at least one outlet is a distance from the proximal end.

3. The medical device of claim 1, wherein the at least one outlet comprises a plurality of side ports at various distances from the proximal end.

4. The medical device of claim 3, wherein the plurality of side ports are angled.

5. The medical device of claim 1, wherein the cannulated probe is rigid.

6. The medical device of claim 1, wherein the cannulated probe is flexible.

7. The medical device of claim 1, wherein the lumen is flexibly shapeable about the soft tissue.

8. The medical device of claim 1, wherein the cannulated probe has a tip insertable into the tear.

9. The medical device of claim 1, wherein the stop extends radially about the cannulated probe to define a support disposable about the surface of the soft tissue.

10. The medical device of claim 1, wherein the stop defines a penetration depth of the delivery portion of the cannulated probe.

11. The medical device of claim 10, wherein the penetration depth is configured to span positions of the soft tissue on either side of the tear.

12. The medical device of claim 1, wherein the stop is shaped to cover the tear and seal the adhesive therein.

13. The medical device of claim 1, further comprising a fiber optic cable disposable through the lumen.

14. The medical device of claim 1, wherein:
    the stop forms an external diameter around the tubular wall of the probe; and
    the stop is adjustable to extend radially from the tubular probe at an angle such that the stop is flush with a surface of the tissue.

15. A method of repairing soft tissue, comprising:
    providing the medical device of claim 1;
    inserting the cannulated probe into the soft tissue;
    passing the adhesive through the lumen and into the tear; and
    retracting the cannulated probe from the soft tissue.

16. A system for repairing soft tissue, comprising:
    an adhesive stored in an adhesive source; and
    a medical device, comprising:
      a cannulated probe formed from a single tubular wall defining a periphery of the cannulated probe and a single lumen therethrough, the cannulated probe positionable about a tear in the soft tissue, the single tubular wall of the cannulated probe forming a needle configured to penetrate tissue at a distal end, the single tubular wall having an inlet at a proximal end and at least one outlet about the distal end with the single lumen therethrough, the inlet connected to the adhesive source to receive the adhesive therein and deliver the adhesive through the single lumen to the at least one outlet, the at least one outlet positionable about the tear to emit the adhesive about the tear;

a stop adjustably disposed about a periphery of the single tubular wall of the cannulated probe a distance from the inlet, the stop terminating advancement of the cannulated probe into the soft tissue and preventing further insertion when a delivery portion of the cannulated probe is positioned about the soft tissue to deliver the adhesive about the tear; and a v-shaped clip comprising an upper plate and a lower plate hingedly connected to the upper plate to define an opening to receive the soft tissue therein and grasp the soft tissue therebetween, wherein the upper plate is configured to fit over a planar surface of the soft tissue having the tear and the lower plate is configured to fit over an opposing planar surface of the soft tissue opposite the tear to secure the opposing planar sides of the tissue, the cannulated probe disposable through the v-shaped clip, wherein the single lumen extends the length of the single tubular wall of the cannulated probe between the inlet and the outlet.

17. The system of claim 16, wherein the adhesive comprises at least one of chemical agents selected from the group of anesthetic agents, plasticizing agents, therapeutic agents, buffers, catalysts, fillers, micro particles, adhesion initiators, thickeners, solvents, drugs, medicaments, natural rubbers, synthetic rubbers, stabilizers, pH modifiers, bioactive agents, cross-linking agents, chain transfer agents, fibrous reinforcements, colorants, preservatives, reducing agents, scavenging agents, formaldehydes, and mixtures thereof.

18. The system of claim 16, wherein the adhesive comprises at least one of polylactide, poylglycolide, polysaccharides, certain proteins, polyesters, polyhydroxyal kanoates, polyalkelene esters, polyamides, polycaprolactone, polyvinyl esters, polyamide esters, polyvinyl alcohols, polyanhydrides and their copolymers, modified derivatives of caprolactone polymers, polytrimethylene carbonate, polyacrylates, polyethylene glycol, polyolefin, engineered materials, hydrogels, photo-curable hydrogels, terminal diols, minerals, and combinations thereof.

19. The system of claim 16, further comprising a bioabsorbable fiber and a bioabsorbable polymer matrix comprising minerals and therapeutics.

20. A method of repairing soft tissue, comprising:
providing a cannulated probe formed from a single tubular wall defining a periphery of the cannulated probe and a single lumen therethrough, the single tubular wall of the cannulated probe forming a needle configured to penetrate tissue at a distal end, the single tubular wall having an inlet at a proximal end and at least one outlet about the distal end with the single lumen extending the length of the single tubular wall of the cannulated probe between the inlet and the outlet;

providing a v-shaped clip comprising an upper plate and a lower plate hingedly connected to the upper plate to define an opening;

disposing an adjustable stop about a periphery of the single tubular wall of the cannulated probe a distance from the inlet;

placing the upper plate over a first planar surface of the soft tissue having a tear;

placing the lower plate over a second planar surface of the soft tissue, the second planar surface opposite the first planar surface, such that the v-shaped clip grasps the soft tissue between the upper plate and the lower plate;

positioning the cannulated probe through the upper plate and about the tear in the soft tissue;

after disposing the adjustable stop about the periphery, advancing the cannulated probe until the stop is positioned about the soft tissue and terminates advancement of the cannulated probe preventing further insertion; and delivering an adhesive about the tear by passing the adhesive from the inlet, through the lumen, and out the at least one outlet.

21. The method of claim 20, wherein the positioning comprises inserting a tip of the cannulated probe into the tear.

22. The method of claim 20, wherein the positioning comprises passing the cannulated probe through the tear by inserting a tip of the cannulated probe through the soft tissue on either side of the tear.

23. The method of claim 20, wherein the delivering comprises passing the adhesive out a plurality of the at least one outlet and into the tear.

24. The method of claim 20, further comprising sealing the tear with the stop.

25. The method of claim 20, further comprising disposing a fiber optic through the cannulated probe and visualizing the soft tissue.

26. The method of claim 20, further comprising retracting the cannulated probe from the soft tissue.

27. The method of claim 20, further comprising bridging the tear by extending the cannulated probe through soft tissue on either side of the tear.

* * * * *